US012648853B2

(12) United States Patent
Hunt et al.

(10) Patent No.: US 12,648,853 B2
(45) Date of Patent: Jun. 9, 2026

(54) SACROILIAC JOINT FUSION SYSTEMS AND METHODS

(71) Applicant: 4WEB, LLC, Dallas, TX (US)

(72) Inventors: Jessee Hunt, Plano, TX (US); Dave Matusz, New York, NY (US)

(73) Assignee: 4WEB, LLC, Dallas, TX (US)

( * ) Notice: Subject to any disclaimer, the term of this patent is extended or adjusted under 35 U.S.C. 154(b) by 900 days.

(21) Appl. No.: 17/210,413

(22) Filed: Mar. 23, 2021

(65) Prior Publication Data

US 2021/0228360 A1 Jul. 29, 2021

Related U.S. Application Data

(63) Continuation-in-part of application No. 17/085,407, filed on Oct. 30, 2020, and a continuation-in-part of
(Continued)

(51) Int. Cl.
*A61F 2/28* (2006.01)
*A61F 2/30* (2006.01)
(Continued)

(52) U.S. Cl.
CPC .............. *A61F 2/28* (2013.01); *A61F 2/2803* (2013.01); *A61F 2/30* (2013.01); *A61F 2/30907* (2013.01); *A61F 2/30942* (2013.01); *A61F 2/32* (2013.01); *A61F 2/38* (2013.01); *A61F 2/4202* (2013.01); *A61F 2/4225* (2013.01); *A61F 2/44* (2013.01); *A61F 2/4455* (2013.01); *A61F 2/4465* (2013.01); *A61F*

*2/447* (2013.01); *A61F 2/4611* (2013.01); *A61F 2002/2835* (2013.01); *A61F 2002/3014* (2013.01);
(Continued)

(58) Field of Classification Search
CPC .......... A61F 2/28; A61F 2/30; A61F 2/30907; A61F 2/30942; A61F 2/44; A61F 2/447; A61F 2/4455; A61F 2/46; A61F 2/4611; A61F 2/38; A61F 2/42; A61F 2/4202
See application file for complete search history.

(56) References Cited

U.S. PATENT DOCUMENTS

| | | | |
|---|---|---|---|
| 3,840,904 A | 10/1974 | Tronzo | |
| 3,867,728 A | 2/1975 | Stubstad et al. | |

(Continued)

FOREIGN PATENT DOCUMENTS

| | | | |
|---|---|---|---|
| CN | 201164511 | 12/2008 | |
| CN | 201200499 | 3/2009 | |

(Continued)

OTHER PUBLICATIONS

International Search Report and Written Opinion for PCT/US2020/60759 issued Feb. 17, 2021.
(Continued)

*Primary Examiner* — Christopher J Beccia

(74) *Attorney, Agent, or Firm* — KOWERT, HOOD, MUNYON, RANKIN & GOETZEL, P.C.; Gareth M. Sampson

(57) ABSTRACT

A sacroiliac joint implant is formed from a web structure having a space truss with two or more planar truss units having a plurality of struts joined at nodes. The web structure is configured for fusion of a sacroiliac joint.

30 Claims, 22 Drawing Sheets

Related U.S. Application Data application No. 15/991,272, filed on May 29, 2018, now Pat. No. 10,849,756, which is a continuation of application No. 15/695,122, filed on Sep. 5, 2017, now Pat. No. 9,987,137, which is a continuation of application No. 15/057,195, filed on Mar. 1, 2016, now Pat. No. 9,757,235, which is a continuation of application No. 14/036,974, filed on Sep. 25, 2013, now Pat. No. 9,271,845.

(60) Provisional application No. 62/993,600, filed on Mar. 23, 2020, provisional application No. 62/935,939, filed on Nov. 15, 2019, provisional application No. 62/927,682, filed on Oct. 30, 2019, provisional application No. 61/801,597, filed on Mar. 15, 2013, provisional application No. 61/705,403, filed on Sep. 25, 2012.

(51) Int. Cl.

| | |
|---|---|
| *A61F 2/32* | (2006.01) |
| *A61F 2/38* | (2006.01) |
| *A61F 2/42* | (2006.01) |
| *A61F 2/44* | (2006.01) |
| *A61F 2/46* | (2006.01) |

(52) U.S. Cl.
CPC ............... *A61F 2002/30143* (2013.01); *A61F 2002/30153* (2013.01); *A61F 2002/30156* (2013.01); *A61F 2002/30158* (2013.01); *A61F 2002/30179* (2013.01); *A61F 2002/30273* (2013.01); *A61F 2002/30275* (2013.01); *A61F 2002/3028* (2013.01); *A61F 2002/30281* (2013.01); *A61F 2002/30593* (2013.01); *A61F 2002/30599* (2013.01); *A61F 2002/30841* (2013.01); *A61F 2002/30891* (2013.01); *A61F 2002/30906* (2013.01); *A61F 2002/30909* (2013.01); *A61F 2002/30914* (2013.01); *A61F 2002/3092* (2013.01); *A61F 2002/3093* (2013.01); *A61F 2002/30943* (2013.01); *A61F 2002/30952* (2013.01); *A61F 2002/30953* (2013.01); *A61F 2002/30957* (2013.01); *A61F 2002/30962* (2013.01); *A61F 2002/30968* (2013.01); *A61F 2002/3097* (2013.01); *A61F 2002/30985* (2013.01); *A61F 2310/00017* (2013.01); *A61F 2310/00023* (2013.01); *A61F 2310/00029* (2013.01); *A61F 2310/00047* (2013.01); *A61F 2310/00179* (2013.01); *A61F 2310/00598* (2013.01); *A61F 2310/00796* (2013.01); *A61F 2310/00958* (2013.01); *A61F 2310/0097* (2013.01); *A61F 2310/00976* (2013.01)

(56) References Cited

U.S. PATENT DOCUMENTS

| | | | |
|---|---|---|---|
| 4,129,903 | A | 12/1978 | Huggler |
| 4,686,970 | A | 8/1987 | Dove et al. |
| 4,820,305 | A | 4/1989 | Harms et al. |
| 4,863,474 | A | 9/1989 | Brown et al. |
| 4,904,261 | A | 2/1990 | Dove et al. |
| 4,938,771 | A | 7/1990 | Vecsei et al. |
| 5,030,233 | A | 7/1991 | Ducheyne |
| 5,108,435 | A | 4/1992 | Gustavson et al. |
| 5,147,402 | A | 9/1992 | Bohler et al. |
| 5,201,768 | A | 4/1993 | Caspari et al. |
| 5,282,861 | A | 2/1994 | Kaplan |
| 5,306,149 | A | 4/1994 | Schmid et al. |
| 5,336,266 | A | 8/1994 | Caspari et al. |
| 5,433,750 | A | 7/1995 | Gradinger et al. |
| 5,571,185 | A | 11/1996 | Schug |
| 5,609,635 | A | 3/1997 | Michelson |
| 5,609,637 | A | 3/1997 | Biedermann et al. |
| 5,676,700 | A | 10/1997 | Black et al. |
| 5,702,449 | A | 12/1997 | McKay |
| 5,702,451 | A | 12/1997 | Biedermann et al. |
| 5,879,385 | A | 3/1999 | Crockard et al. |
| 5,897,556 | A | 4/1999 | Drewry et al. |
| 5,954,504 | A | 9/1999 | Misch et al. |
| 5,989,290 | A | 11/1999 | Biedermann et al. |
| 6,010,502 | A | 1/2000 | Bagby |
| 6,090,732 | A | 7/2000 | Ita et al. |
| 6,143,032 | A | 11/2000 | Schafer et al. |
| 6,149,689 | A | 11/2000 | Grundei et al. |
| 6,206,924 | B1 | 3/2001 | Timm |
| 6,245,108 | B1 | 6/2001 | Biscup |
| 6,245,110 | B1 | 6/2001 | Grundei et al. |
| 6,264,695 | B1 | 7/2001 | Stoy |
| 6,280,478 | B1 | 8/2001 | Richter et al. |
| 6,290,726 | B1 | 9/2001 | Pope et al. |
| 6,379,385 | B1 | 4/2002 | Kalas et al. |
| 6,464,727 | B1 | 10/2002 | Sharkey et al. |
| 6,520,997 | B1 | 2/2003 | Pekkarinen et al. |
| 6,585,770 | B1 | 7/2003 | White et al. |
| 6,660,041 | B1 | 12/2003 | Grundei |
| 6,712,852 | B1 | 3/2004 | Chung et al. |
| 6,730,252 | B1 | 5/2004 | Teoh et al. |
| D493,533 | S | 7/2004 | Blain |
| 6,761,738 | B1 | 7/2004 | Boyd |
| 6,866,682 | B1 | 3/2005 | An et al. |
| 6,881,228 | B2 | 4/2005 | Zdeblick et al. |
| 6,931,812 | B1 | 8/2005 | Lipscomb |
| 6,972,019 | B2 | 12/2005 | Michelson |
| 7,156,874 | B2 | 1/2007 | Paponneau et al. |
| 7,163,560 | B2 | 1/2007 | Mason |
| 7,163,561 | B2 | 1/2007 | Michelson |
| 7,208,222 | B2 | 4/2007 | Rolfe et al. |
| 7,291,149 | B1 | 11/2007 | Michelson |
| 7,537,616 | B1 | 5/2009 | Branch et al. |
| 7,572,293 | B2 | 8/2009 | Rhodes et al. |
| 7,578,850 | B2 | 8/2009 | Kuczynski et al. |
| 7,621,950 | B1 | 11/2009 | Globerman et al. |
| 7,846,296 | B2 | 12/2010 | Oglaza et al. |
| 8,062,365 | B2 | 11/2011 | Schwab |
| 8,292,967 | B2 | 10/2012 | Brown et al. |
| 8,430,930 | B2 | 4/2013 | Hunt |
| 8,906,074 | B2 | 12/2014 | Kang |
| 8,998,990 | B2 | 4/2015 | Bertagnoli et al. |
| 9,271,845 | B2 | 3/2016 | Hunt |
| 9,421,108 | B2 | 8/2016 | Hunt |
| 9,545,317 | B2 | 1/2017 | Hunt |
| 9,549,823 | B2 | 1/2017 | Hunt |
| 9,572,669 | B2 | 2/2017 | Hunt |
| 9,636,226 | B2 | 5/2017 | Hunt |
| 9,757,235 | B2 | 9/2017 | Hunt |
| 9,968,463 | B2 | 5/2018 | Liu |
| 9,987,137 | B2 | 6/2018 | Hunt |
| 9,999,516 | B2 | 6/2018 | Hunt |
| 2002/0169066 | A1 | 11/2002 | Cassidy et al. |
| 2002/0183858 | A1 | 12/2002 | Contiliano et al. |
| 2003/0078660 | A1 | 4/2003 | Clifford et al. |
| 2004/0082999 | A1 | 4/2004 | Mathys et al. |
| 2004/0121451 | A1 | 6/2004 | Mortiz et al. |
| 2004/0236336 | A1 | 11/2004 | Foerster |
| 2004/0252382 | A1 | 12/2004 | Nagata |
| 2005/0004572 | A1 | 1/2005 | Biedermann et al. |
| 2005/0015154 | A1 | 1/2005 | Lindsey et al. |
| 2005/0033425 | A1 | 2/2005 | Schwab |
| 2005/0090900 | A1 | 4/2005 | Nordquist |
| 2005/0129726 | A1 | 6/2005 | Liebschner |
| 2005/0143827 | A1 | 6/2005 | Globerman et al. |
| 2005/0171613 | A1 | 8/2005 | Sartorius et al. |
| 2005/0222683 | A1 | 10/2005 | Berry |
| 2006/0015105 | A1* | 1/2006 | Warren ................ A61B 17/746 |
| | | | 606/301 |
| 2006/0074488 | A1 | 4/2006 | Abdou |
| 2006/0106461 | A1 | 5/2006 | Embry et al. |
| 2006/0147332 | A1 | 7/2006 | Jones et al. |

(56) References Cited

U.S. PATENT DOCUMENTS

| | | |
|---|---|---|
| 2006/0200062 A1 | 9/2006 | Saadat |
| 2006/0241776 A1 | 10/2006 | Brown et al. |
| 2007/0027544 A1 | 2/2007 | McCord et al. |
| 2007/0032876 A1 | 2/2007 | Clark |
| 2007/0040478 A1 | 2/2007 | Tofail et al. |
| 2007/0055376 A1 | 3/2007 | Michelson |
| 2007/0083268 A1 | 4/2007 | Teoh et al. |
| 2007/0106383 A1 | 5/2007 | Abdou |
| 2007/0129806 A1 | 6/2007 | Harms et al. |
| 2007/0179610 A1 | 8/2007 | Biedermann et al. |
| 2007/0191834 A1 | 8/2007 | Bruneau et al. |
| 2007/0233248 A1 | 10/2007 | Schwab et al. |
| 2007/0255420 A1 | 11/2007 | Johnson et al. |
| 2007/0255422 A1 | 11/2007 | Wei et al. |
| 2007/0270956 A1 | 11/2007 | Heinz |
| 2008/0014457 A1 | 1/2008 | Gennaro et al. |
| 2008/0021461 A1 | 1/2008 | Barker et al. |
| 2008/0039948 A1 | 2/2008 | Biedermann et al. |
| 2008/0071356 A1 | 3/2008 | Greenhalgh et al. |
| 2008/0075752 A1 | 3/2008 | Ratner et al. |
| 2008/0154314 A1 | 6/2008 | McDevitt |
| 2008/0183204 A1 | 7/2008 | Greenhalgh et al. |
| 2008/0221594 A1 | 9/2008 | Hamman et al. |
| 2009/0054987 A1 | 2/2009 | Chin |
| 2009/0076508 A1 | 3/2009 | Weinans et al. |
| 2009/0099610 A1 | 4/2009 | Johnson et al. |
| 2009/0138015 A1 | 5/2009 | Conner et al. |
| 2009/0149947 A1 | 6/2009 | Frohwitter |
| 2009/0149956 A1 | 6/2009 | Greenhalgh et al. |
| 2009/0182336 A1 | 7/2009 | Brenzel et al. |
| 2009/0222098 A1 | 9/2009 | Trieu et al. |
| 2009/0228112 A1 | 9/2009 | Clark et al. |
| 2009/0276048 A1 | 11/2009 | Chirico et al. |
| 2009/0317447 A1 | 12/2009 | Hsiao et al. |
| 2009/0326657 A1 | 12/2009 | Grinberg |
| 2010/0094292 A1 | 4/2010 | Parrott |
| 2010/0106194 A1 | 4/2010 | Bonutti |
| 2010/0161061 A1 | 6/2010 | Hunt |
| 2010/0174377 A1 | 7/2010 | Heuer |
| 2010/0174380 A1 | 7/2010 | Lewis |
| 2010/0179667 A1 | 7/2010 | Day et al. |
| 2010/0228355 A1 | 9/2010 | Linares |
| 2010/0298950 A1 | 11/2010 | McDonnel et al. |
| 2011/0022180 A1 | 1/2011 | Melkent et al. |
| 2011/0035020 A1 | 2/2011 | Laughner et al. |
| 2011/0076316 A1 | 3/2011 | Sivananthan et al. |
| 2011/0118852 A1 | 5/2011 | Evans |
| 2011/0125284 A1 | 5/2011 | Gabbrielli et al. |
| 2011/0196495 A1 | 8/2011 | Hunt |
| 2011/0218585 A1 | 9/2011 | Krinke |
| 2011/0251690 A1 | 10/2011 | Berger |
| 2011/0264229 A1 | 10/2011 | Donner |
| 2011/0307073 A1 | 12/2011 | Teoh et al. |
| 2011/0313532 A1 | 12/2011 | Hunt |
| 2012/0191191 A1* | 7/2012 | Trieu ................... A61B 17/864 |
| | | 623/17.11 |
| 2012/0290089 A1 | 11/2012 | Melamed |
| 2013/0030529 A1 | 1/2013 | Hunt |
| 2013/0030540 A1 | 1/2013 | Leibinger |
| 2013/0123935 A1 | 5/2013 | Hunt |
| 2013/0158672 A1 | 6/2013 | Hunt |
| 2013/0184835 A1 | 7/2013 | Ferrari et al. |
| 2013/0218282 A1 | 8/2013 | Hunt |
| 2014/0121776 A1 | 5/2014 | Hunt |
| 2014/0277569 A1 | 9/2014 | Lange |
| 2014/0288649 A1 | 9/2014 | Hunt |
| 2014/0288650 A1 | 9/2014 | Hunt |
| 2015/0282933 A1 | 10/2015 | Hunt |
| 2015/0282945 A1 | 10/2015 | Hunt |
| 2015/0282946 A1 | 10/2015 | Hunt |
| 2016/0081807 A1 | 3/2016 | Estes et al. |
| 2016/0143671 A1* | 5/2016 | Jimenez ............. A61B 17/7082 |
| | | 606/304 |
| 2016/0287389 A1 | 10/2016 | Hunt |
| 2016/0287404 A1 | 10/2016 | Hunt |
| 2016/0287405 A1 | 10/2016 | Hunt |
| 2016/0302941 A1* | 10/2016 | Reiley ............... A61B 17/7055 |
| 2016/0338842 A1 | 11/2016 | Adams |
| 2017/0157299 A1 | 6/2017 | Janko et al. |
| 2017/0216035 A1 | 8/2017 | Hunt |
| 2017/0296244 A1* | 10/2017 | Schneider ............. A61B 17/84 |
| 2017/0319344 A1 | 11/2017 | Hunt |
| 2017/0360563 A1 | 12/2017 | Hunt |
| 2018/0064540 A1 | 3/2018 | Hunt |
| 2018/0085230 A1 | 3/2018 | Hunt |
| 2019/0060077 A1 | 2/2019 | Hunt |
| 2019/0151114 A1 | 5/2019 | Sack |
| 2020/0155326 A1 | 5/2020 | Hunt |

FOREIGN PATENT DOCUMENTS

| | | |
|---|---|---|
| DE | 19543530 | 5/1997 |
| DE | 19721661 | 11/1998 |
| DE | 10120330 A1 | 11/2002 |
| DE | 202006015414 U1 | 11/2006 |
| DE | 202006015415 U1 | 11/2006 |
| DE | 102006047663 | 4/2008 |
| DE | 102018105915 | 9/2019 |
| EP | 0396883 A2 | 11/1990 |
| EP | 0268115 | 1/1991 |
| EP | 0489684 | 6/1992 |
| EP | 0561263 | 9/1993 |
| EP | 1925271 A1 | 5/2008 |
| JP | 52-148995 | 12/1977 |
| JP | Hei06-503990 | 5/1994 |
| JP | 2002-536046 | 10/2002 |
| JP | 2003-511198 | 3/2003 |
| JP | 2007-167665 | 7/2007 |
| JP | 2008-539817 | 11/2008 |
| JP | 2009-006186 | 1/2009 |
| JP | 2009112719 | 5/2009 |
| JP | 2012520120 | 9/2012 |
| WO | 2001028460 | 4/2001 |
| WO | 02071986 A2 | 9/2002 |
| WO | 2005009729 | 2/2005 |
| WO | 2007048817 A1 | 5/2007 |
| WO | 2008022206 | 2/2008 |
| WO | 2008146141 A2 | 12/2008 |
| WO | 2009144434 | 12/2009 |
| WO | 2010080511 | 7/2010 |
| WO | 2012010327 | 1/2012 |
| WO | 2013006778 | 1/2013 |

OTHER PUBLICATIONS

International Search Report and Written Opinion for PCT/US2021/023782 issued Jul. 1, 2021.

Office Action for U.S. Appl. No. 13/762,825 issued Mar. 7, 2016.

Office Action for U.S. Appl. No. 13/762,825 issued Sep. 20, 2016.

International Search Report and Written Opinion for PCT/US2013/025281 issued May 15, 2013.

International Preliminary Report on Patentability for PCT/US2013/025281 issued Aug. 12, 2014.

Australian Examination Report for AU Application No. 2013216947 dated Mar. 27, 2017.

Australian Examination Report for AU Application No. 2013216947 dated Feb. 16, 2018.

Canadian Examination Report for CA Application No. 2,863,865 dated Oct. 5, 2018.

Canadian Examination Report for CA Application No. 2,863,865 dated Jun. 5, 2020.

European Examination Report for EP Application No. 13746753.6 dated Sep. 23, 2015.

European Examination Report for EP Application No. 13746753.6 dated Oct. 28, 2016.

Japanese Examination Report for JP Application No. 2014-556705 dated Nov. 29, 2016.

Japanese Examination Report for JP Application No. 2014-556705 dated Sep. 19, 2017.

Office Action for U.S. Appl. No. 15/463,458 issued Dec. 26, 2017.

(56)          References Cited

OTHER PUBLICATIONS

Final Office Action for U.S. Appl. No. 15/463,458 issued Oct. 24, 2018.
Japanese Examination Report for JP Application No. 2018-006991 dated Nov. 20, 2018.
Japanese Examination Report for JP Application No. 2018-006991 dated Nov. 12, 2019.
Australian Examination Report for AU Application No. 2018202175 dated Nov. 22, 2018.
Australian Examination Report for AU Application No. 2018202175 dated Aug. 23, 2019.
Office Action for U.S. Appl. No. 14/036,974 issued Jul. 22, 2015.
International Search Report and Written Opinion for PCT/US2013/061725 issued Jan. 13, 2014.
International Preliminary Report on Patentability for PCT/US2013/061725 issued Mar. 13, 2015.
Canadian Examination Report for CA Application No. 2,889,063 dated Sep. 20, 2019.
Canadian Examination Report for CA Application No. 2,889,063 dated Jul. 31, 2020.
Chinese Examination Report for CN Application No. 20130055597.3 dated Apr. 5, 2016.
Chinese Examination Report for CN Application No. 20130055597.3 dated Nov. 16, 2016.
Chinese Examination Report for CN Application No. 20130055597.3 dated Jun. 8, 2017.
Extended European Search Report for European Application No. 13843010.3 dated Apr. 16, 2019.
Third Party Observations for European Application No. 13843010.3 dated Jan. 30, 2020.
Korean Office Action for Korean Application No. 10-2015-7010324 dated May 18, 2020.
Japanese Examination Report for JP Application No. 2013-533302 dated Aug. 15, 2017.
Australian Examination Report for AU Application No. 2013323602 dated Jul. 4, 2017.
Office Action for U.S. Appl. No. 14/215,961 issued Mar. 11, 2016.
International Search Report and Written Opinion for PCT/US2014/030319 issued Apr. 6, 2015.
International Preliminary Report on Patentability for PCT/US2014/030319 issued Sep. 15, 2015.
Office Action for U.S. Appl. No. 14/216,087 issued Aug. 27, 2015.
Office Action for U.S. Appl. No. 14/216,087 issued Jul. 14, 2016.
Office Action for U.S. Appl. No. 14/216,087 issued Feb. 2, 2017.
International Search Report and Written Opinion for PCTUS201430358 issued Aug. 27, 2014.
International Preliminary Report on Patentability for PCTUS201430358 issued Sep. 15, 2015.
Canadian Examination Report for CA Application No. 2,911,880 dated Mar. 26, 2021.
Chinese Examination Report for CN Application No. 201480026652.0 dated Dec. 2, 2016.
Chinese Examination Report for CN Application No. 201480026652.0 dated Jul. 31, 2017.
European Examination Report for EP Application No. 14762747 dated Jan. 26, 2017.
Japanese Examination Report for JP Application No. 2016-503373 dated Jan. 29, 2018.
Japanese Examination Report for JP Application No. 2016-503373 dated Dec. 17, 2018.
Korean Office Action for KR Application No. 10-2015-7029384 dated Oct. 22, 2020.
Japanese Examination Report for JP Application No. 2019-147711 dated Jul. 22, 2020.
Office Action issued in Canadian Application No. 2,911,880 dated Mar. 26, 2021.
International Search Report and Written Opinion for PCT/US2020/58330 issued Jan. 29, 2021.
International Search Report and Written Opinion for PCT/US2021/040939 issued Nov. 4, 2021.

Advisory Action for U.S. Appl. No. 15/721,940 issued Mar. 13, 2020.
Office Action for U.S. Appl. No. 15/721,940 issued Jun. 2, 2020.
Office Action for U.S. Appl. No. 12/818,508 issued Feb. 4, 2013.
Final Office Action for U.S. Appl. No. 12/818,508 issued Aug. 15, 2013.
Office Action for U.S. Appl. No. 12/818,508 issued May 22, 2015.
Final Office Action for U.S. Appl. No. 12/818,508 issued Nov. 20, 2015.
Office Action for U.S. Appl. No. 12/818,508 issued Dec. 2, 2016.
EPO International Search Report and Written Opinion for PCT/US2011/040117 mailed Aug. 12, 2011.
International Preliminary Report on Patentability for PCT/US2011/040117 dated Dec. 19, 2012.
Office Action for U.S. Appl. No. 13/805,231 issued Aug. 20, 2015.
Final Office Action for U.S. Appl. No. 13/805,231 issued Dec. 11, 2015.
Office Action for U.S. Appl. No. 13/805,231 issued Oct. 12, 2016.
Final Office Action for U.S. Appl. No. 13/805,231 issued Apr. 25, 2017.
Office Action for U.S. Appl. No. 13/805,231 issued Dec. 18, 2017.
Australian Examination Report for AU Application No. 2011267941 dated Jan. 16, 2014.
Canadian Examination Report for Canadian Patent Application No. 2,803,015 dated Jun. 15, 2017.
Canadian Examination Report for Canadian Patent Application No. 2,803,015 dated Feb. 9, 2018.
Canadian Examination Report for Canadian Patent Application No. 2,803,015 dated Dec. 5, 2019.
Canadian Examination Report for Canadian Patent Application No. 2,803,015 dated Dec. 30, 2020.
European Examination Report for EP Application No. 11726306.1 dated Jan. 7, 2016.
European Examination Report for EP Application No. 11726306.1 dated Nov. 13, 2017.
Japanese Examination Report for JP Application No. 2013-515407 dated Feb. 24, 2015.
Japanese Examination Report for JP Application No. 2013-515407 dated Nov. 24, 2015.
Office Action for U.S. Appl. No. 13/194,561 issued Mar. 19, 2013.
Final Office Action for U.S. Appl. No. 13/194,561 issued Sep. 26, 2013.
Office Action for U.S. Appl. No. 13/194,561 issued Jan. 20, 2015.
International Search Report and Written Opinion for PCT/US2012/048300 May 7, 2013.
International Preliminary Report on Patentability for PCT/US2012/048300 Feb. 4, 2014.
Japanese Examination Report for JP Application No. 2014-523976 dated May 24, 2016.
International Search Report and Written Opinion for PCT/US2012/045717 issued Jan. 30, 2013.
International Preliminary Report on Patentability for PCT/US2012/045717 dated Jan. 7, 2014.
Office Action for U.S. Appl. No. 13/668,968 issued Aug. 18, 2014.
Office Action for U.S. Appl. No. 13/668,968 issued Jan. 7, 2015.
Office Action for U.S. Appl. No. 13/668,968 issued Jun. 29, 2015.
Office Action for U.S. Appl. No. 13/668,968 issued Apr. 14, 2016.
Final Office Action for U.S. Appl. No. 13/668,968 issued Nov. 16, 2016.
International Search Report and Written Opinion for PCT/US2012/063600 issued Jan. 31, 2013.
International Preliminary Report on Patentability for PCT/US2012/063600 issued May 6, 2014.
Australian Examination Report for AU Application No. 2012332092 dated Feb. 14, 2017.
Australian Examination Report for AU Application No. 2012332092 dated Dec. 19, 2017.
Australian Examination Report for AU Application No. 2012332092 dated Feb. 9, 2018.
Canadian Examination Report for Canadian Patent Application No. 2,854,021 dated Jul. 26, 2018.
Supplemental European Search Report for EP Application No. 12846553.1 issued May 20, 2015.

(56) References Cited

OTHER PUBLICATIONS

European Office Action for EP Application No. 12846553.1 issued Mar. 17, 2016.
European Office Action for EP Application No. 12846553.1 issued Aug. 19, 2016.
Japanese Examination Report for JP Application No. 2014-540188 dated Jul. 14, 2016.
Australian Examination Report for AU Application No. 2018201065 dated Jul. 20, 2018.
Australian Examination Report for AU Application No. 2018201065 dated Jul. 3, 2019.
Office Action for U.S. Appl. No. 13/762,825 issued Jul. 2, 2014.
Office Action for U.S. Appl. No. 13/762,825 issued Dec. 12, 2014.
"Rapid prototyping enables company to manufacture revolutionary new medical product", accessed at <http://www.newslettersonline.com/user/user.fas/s=63/fp=3/tp=47?T=open_article,565208&P=article>, Oct. 9, 2003. (pp. 1-2).
"Midlantic Medical Systems—Geo Structure Rectangles (Posterior Approach)" accessed Jun. 11, 2008 at <http://www.midlanticmedical.com/products/anteriorColumnSpacers.php?p=2>. (p. 1).
"Midlantic Medical Systems—Nexus (Transverse Approach)" accessed Jun. 11, 2008 at <http://www.midlanticmedical.com/products/anteriorColumnSpacers.php?p=4>. (p. 1).
"Zimmer® Trabecular Metal™ Technology", accessed at <http://www.zimmerindia.com/z/ctl/op/global/action/1/id/9512template/PC/navid/8173>, Jul. 9, 2006. (pp. 1-5).
"Multifunctional Electrochemical Energy Storage Materials", accessed on Oct. 1, 2008 at <http://www.uvapf.org/technologies/index.cfm/fuseaction/invention/invention_id/85/?CFID=1785971&CFTOKEN=59649784&>. (pp. 1-2).
"Image: C60a.phg", Wikipedia, accessed on Oct. 1, 2008 at <http://en.wikipedia.org/wiki/Image:C60a.png> (pp. 1-3).
"Image:POV-Ray-Dodecahedron.svg", Wikipedia, accessed at on Oct. 1, 2008 at <http://en.wikipedia.org/wiki/Image:POV-Ray-Dodecahedron.svg>. (pp. 1-4).
"Image:Icosahedron.svg", Wikipedia, accessed on Oct. 1, 2008 at <http://en.wikipedia.org/wiki/Image:Icosahedron.svg>. (pp. 1-2).
"Image:Octahedron.svg", Wikipedia, accessed on Oct. 1, 2008 at <http://en.wikipedia.org/wiki/Image:Octahedron.svg>. (pp. 1-3).
"Truss" Wikipedia, accessed at <http://en.wikipedia.org/wiki/Truss>, Dec. 16, 2009. (pp. 1-9).
"NexGen Trabecular Metal Tibial Cone Augments" accessed at <http://catalog.zimmer.com/content/zpc/products/200/250/C60/CE008/2653.html>, Nov. 17, 2009. (p. 1).
"Spinal Kinetics", accessed on Oct. 6, 2009 at <http://www.spinalkinetics.com/m6systems.html>. (p. 1).
"CINN", accessed on Oct. 6, 2009 at <http://www.cinn.org/cr-articles/CR-artificial-disc.html>, Copyright 2008. (pp. 1-9).
"Zimmer Anatomical Shoulder Fracture System", copyright 2007. (pp. 1-6).
"Wolff's Law", Wikipedia, accessed at <http://en.wikipedia.org/wiki/Wolff's_law>, Jun. 9, 2010. (pp. 1-2).
"e-Manufacturing is making its inroad to series production", Nov. 20, 2008. (pp. 1-2).
"InFix Anterior Lumbar Device" Dec. 17, 2009. (p. 1).
"Biofoam Wedge System" Wright, Copyright 2010. (pp. 1-4).
"LPT2 Great Toe Implant" Wright, Copyright 2008. (p. 1-16).
"Biofoam Wedge System Surgical Technique" Wright, Copyright 2010. (pp. 1-12).
Murr et al. "Next-generation biomedical implants using additive manufacturing of complex, cellular and functional mesh arrays", Philosophical Transactions of the Royal Society, Mar. 22, 2010, vol. 368, No. 1917, pp. 1999-2032.
Yan, et al. "Mechanical strain regulates osteoblast proliferation through integrin-mediated ERK activation", PloS One, Apr. 23, 2012, vol. 7, No. 4, Article No. e35709.
Distension Blog located at htpp://kineticdistensio.blogspot.com/2011_10_0_archive.html including entry of Oct. 14, 2011.

Baranovskaya et al. ITECH M. Sc. Programme-Uni Stuttgart, Institut Fur Computerbasiertes Entwerfen (ICD, Stuttgart, Germany located at htpp:/architecture-is-yes.tumblr.com/post/8525760 accessed Aug. 21, 2015.
Cobos et al. "The Cylindrical Titanium Mesh Cage for Treatment of a Long Bone Segmental Defect: Description of a New Technique and Report of Two Cases" Journal of Orthopaedic Trauma (2000) vol. 14, No. 1, pp. 54-59.
Lindsey et al. "The Efficacy of Cylindrical Titanium Mesh Cage for the Reconstruction of a Critical-Size Canine Segmental Remoral Diaphyseal Defect" Journal of Orthopaedic Research (Jul. 2006), pp. 1438-1453.
Office Action for U.S. Appl. No. 12/640,825 issued Aug. 30, 2012.
EPO International Search Report and Written Opinion for PCT/US2009/068512 mailed May 12, 2010. (pp. 1-61).
International Preliminary Report on Patentability for PCT/US2009/068512 dated Mar. 31, 2011. (pp. 1-8).
Office Action for U.S. Appl. No. 12/960,092 issued Aug. 20, 2014.
Office Action for U.S. Appl. No. 12/960,092 issued Apr. 24, 2015.
Australian Examination Report for Australian Patent Application No. 2009335771 dated Jan. 14, 2014.
Canadian Examination Report for Canadian Patent Application No. 2,746,505 dated Dec. 1, 2015.
European Examination Report for EP Application No. 09796208.8 dated Feb. 7, 2014.
European Examination Report for EP Application No. 09796208.8 dated Aug. 21, 2014.
Office Action for U.S. Appl. No. 14/743,555 issued Sep. 27, 2016.
Final Office Action for U.S. Appl. No. 14/743,555 issued Jul. 3, 2017.
Office Action for U.S. Appl. No. 14/743,579 issued Apr. 5, 2016.
Office Action for U.S. Appl. No. 14/743,607 issued Apr. 6, 2016.
Final Office Action for U.S. Appl. No. 14/743,607 issued Sep. 12, 2016.
Office Action for U.S. Appl. No. 14/743,607 issued Jun. 7, 2017.
Final Office Action for U.S. Appl. No. 14/743,607 issued Apr. 6, 2018.
Office Action for U.S. Appl. No. 14/743,607 issued Dec. 14, 2018.
Final Office Action for U.S. Appl. No. 14/743,607 issued Jun. 10, 2019.
Office Action for U.S. Appl. No. 14/743,607 issued Jan. 13, 2020.
Final Office Action for U.S. Appl. No. 14/743,607 issued Aug. 4, 2020.
Australian Examination Report for Australian Patent Application No. 2013323602 dated Jul. 4, 2017.
Office Action for U.S. Appl. No. 15/721,940 issued Jun. 29, 2018.
Office Action for U.S. Appl. No. 15/721,940 issued Mar. 26, 2019.
Final Office Action for U.S. Appl. No. 15/721,940 issued Oct. 16, 2019.
Rosen, Dr. David, et al., Design of General Lattice Structures for Lightweight and Compliance Applications, Jul. 5, 2006, Rapid Manufacturing Conference, Loughborough University, Jul. 5-6, 2006, 14 pgs.
HRL Announces Extraordinary New Lightweight Materials, HRL Laboratories | News, Oct. 29, 2007, 2 pgs.
Lefebvre, Louis-Philippe, et al., Porous Metals and Metallic Foams: Current Status and Recent Developments, Sep. 17, 2008, Advanced Engineering Materials 2008, 10, No. 9, pp. 775-787.
European Search Report for EP Application No. 21 77 5059 issued Apr. 11, 2024, 9 pgs.
Office Action for EP Patent Application No. 21 77 5059 issued Sep. 2, 2025, 9 pgs.
Examination Report for Australian Patent Application No. 2021244477 issued Jul. 30, 2025, 9 pgs.
Ho Allen Let Al: "Grade II Spondylolisthesis: Reverse Bohlman Procedure with Transdiscal S1-L5 and S2 Alar Iliac Screws Placed with Robotic Guidance", World Neurosurgery, Elsevier, Amsterdam, NL, vol. 132, Aug. 6, 2019 (Aug. 6, 2019), p. 421, XP085911904, ISSN: 1878-8750, DOI: 10.1016/J.WNEU.2019.07.229 [retrieved on Aug. 6, 2019].
Examination Report No. 2 for Australian Patent Application No. 2021244477, issued Dec. 4, 2025, 3 pgs.

(56) References Cited

OTHER PUBLICATIONS

Notice of Acceptance for Australian Patent Application No. 2021244477, issued Mar. 12, 2026, 3 pgs.
Communication pursuant to Article 94(3) EPC dated Mar. 19, 2026, issued by the European Patent Office for European Patent Application No. 21 775 059.5, dated Mar. 19, 2026, 8 pp.

\* cited by examiner

Start Point for S2AI Screw Identified
1710

Create Posterior Breach
1720

Insert k-Wire
1730

Tap Point Hole
1740

Form Channel Over Sacrum And Into Ilium
1750

Palpate Channel
1760

Create Tract for Implant Placement
1770

Select Implant
1780

Place Implant In Channel
1790

Insert Fastener(s)
1795

SACROILIAC JOINT FUSION SYSTEMS AND METHODS

PRIORITY CLAIM

This application claims priority to U.S. Provisional Application Ser. No. 62/993,600 filed Mar. 23, 2020, which is incorporated herein by reference in its entirety. This application is a continuation-in-part of U.S. patent application Ser. No. 17/085,407 filed Oct. 30, 2020, which claims priority to U.S. Provisional Application Ser. No. 62/935,939 filed Nov. 15, 2019 and U.S. Provisional Application Ser. No. 62/927,682 filed Oct. 30, 2019 and is a continuation-in-part of U.S. patent application Ser. No. 15/991,272 filed May 29, 2018, which is a continuation of U.S. patent application Ser. No. 15/695,122 filed Sep. 5, 2017, which is a continuation of U.S. patent application Ser. No. 15/057,195 filed Mar. 1, 2016, which is a continuation of U.S. patent application Ser. No. 14/036,974 filed Sep. 25, 2013, which claims priority to U.S. Provisional Application Ser. No. 61/801,597 filed Mar. 15, 2013 and U.S. Provisional Application Ser. No. 61/705,403 filed Sep. 25, 2012, each of which is incorporated by reference in its entirety.

BACKGROUND

1. Field of the Invention

The present invention relates generally to medical devices and methods, more specifically, to devices and methods related to sacroiliac joint fusion.

2. Description of the Related Art

The sacroiliac joint (SI joint) provides a link between the sacrum (located at the lowest part of the spine) and the ilium bones of the pelvis. The SI joint is formed by a combination of cartilage and ligaments. Inflammation of the SI joint ligaments and/or degradation of the cartilage can cause significant pain to subjects.

The standard treatment for SI joint pain is a sacroiliac joint fusion. This procedure is designed to eliminate movement of the SI joint by fusing together the ilium and sacrum. Typically, sacroiliac fusion relies on the user of screws or rods that are implanted across the SI joint. The screws or rods hold the bones together allowing the bones to fuse. In some instances, a bone graft material is inserted into the interface between the ilium and sacrum bones to promote bone fusion.

SUMMARY

Various embodiments of implant systems and related apparatus, and methods of operating the same are described herein. In various embodiments, an implant for interfacing with a bone structure includes a geometric structure configured to interface with human bone tissue.

In an embodiment, an implant apparatus for interfacing with a bone structure, includes: an implant configured to interface with human bone tissue where the implant is configured to be placed in a channel formed in a sacrum bone of the subject; and an opening formed longitudinally through the implant. A fastener is configured to be inserted through the subject's sacrum bone and into the opening of the implant where a distal end of the fastener purchases in bone tissue. In some embodiments, a locking mechanism is configured to be coupled to a proximal end of the fastener where the locking mechanism secures the proximal end of the fastener to the implant.

In an embodiment, a method of repairing a sacroiliac joint in a subject, includes obtaining an implant having an opening formed longitudinally through the implant. A channel is formed in a sacrum bone of the subject and the implant is placed into the channel. A fastener may then be inserted through the subject's sacrum bone and into the opening of the implant where a distal end of the fastener purchases in bone tissue.

BRIEF DESCRIPTION OF THE DRAWINGS

A better understanding of the present invention may be obtained when the following detailed description is considered in conjunction with the following drawings, in which:

FIGS. 4A-4B illustrate a top structure of an internal web structure of the implant, according to an embodiment.

FIG. 1l depicts the implant of FIGS. 10A-C coupled to an external support.

Figure 1A:
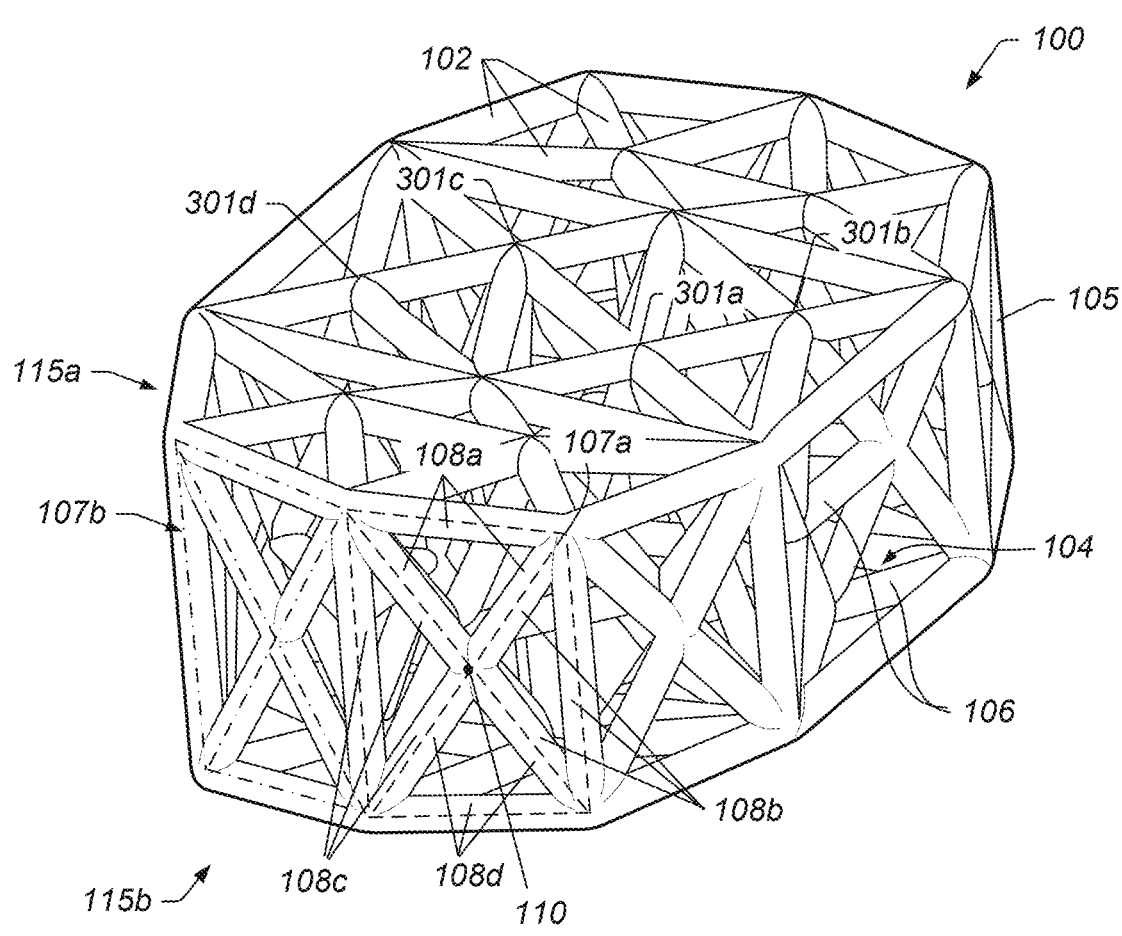
FIGS. 1A-1B illustrate views of an implant with lordosis, according to an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION OF THE EMBODIMENTS

Figure 1B:
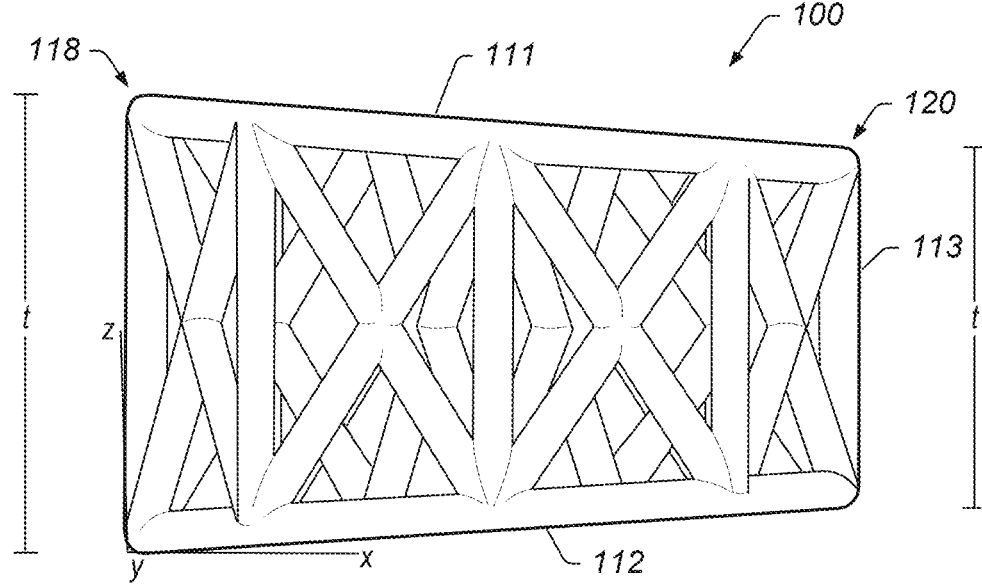

FIGS. 1A-1B illustrate views of implant 100, according to an embodiment. The specifically depicted implant 100 may be used, for example, in anterior lumbar inter-body fusion (ALIF) or posterior lumbar inter-body fusion (PLIF), however, it should be understood that implant 100 may have a variety of shapes suitable for any bone fusion application (e.g., SI joint fusion). In some embodiments, implant 100 may include a web structure with one or more trusses 102 (e.g., planar and space trusses). Implant 100 may be used in various types of implants for humans or animals such as spinal implants, corpectomy devices, knee replacements, hip replacements, long bone reconstruction scaffolding, and cranio-maxiofacial implants. Other implant uses are also contemplated.

As used herein a "truss structure" is a structure having one or more elongate struts connected at joints referred to as nodes. Trusses may include variants of a pratt truss, king post truss, queen post truss, town's lattice truss, planar truss, space truss, and/or a vierendeel truss (other trusses may also be used). A "truss unit" is a structure having a perimeter defined by three or more elongate struts."

As used herein a "planar truss" is a truss structure where all of the struts and nodes lie substantially within a single two-dimensional plane. A planar truss, for example, may include one or more "truss units" where each of the struts is a substantially straight member such that the entirety of the struts and the nodes of the one or more truss units lie in substantially the same plane. A truss unit where each of the struts is a substantially straight strut and the entirety of the struts and the nodes of the truss unit lie in substantially the same plane is referred to as a "planar truss unit."

As used herein a "space truss" is a truss having struts and nodes that are not substantially confined in a single two-dimensional plane. A space truss may include two or more planar trusses (e.g., planar truss units) wherein at least one of the two or more planar trusses lies in a plane that is not substantially parallel to a plane of at least one or more of the other two or more planar trusses. A space truss, for example, may include two planar truss units adjacent to one another (e.g., sharing a common strut) wherein each of the planar truss units lie in separate planes that are angled with respect to one another (e.g., not parallel to one another).

As used herein a "triangular truss" is a structure having one or more triangular units that are formed by three straight struts connected at joints referred to as nodes. For example, a triangular truss may include three straight elongate strut members that are coupled to one another at three nodes to from a triangular shaped truss. As used herein a "planar triangular truss" is a triangular truss structure where all of the struts and nodes lie substantially within a single two-dimensional plane. Each triangular unit may be referred to as a "triangular truss unit." A triangular truss unit where each of the struts is a substantially straight member such that the entirety of the struts and the nodes of the triangular truss units lie in substantially the same plane is referred to as a "planar triangular truss unit." As used herein a "triangular space truss" is a space truss including one or more triangular truss units.

In various embodiments, the trusses 102 of the web structure may include one or more planar truss units (e.g., planar triangular truss units) constructed with straight or curved/arched members (e.g., struts) connected at various nodes. In some embodiments, the trusses 102 may be micro-trusses. A "micro-truss" is a truss having dimensions sufficiently small enough such that a plurality of micro-trusses can be assembled or otherwise coupled to one another to form a web structure having a small enough overall dimension (e.g., height, length and width) such that substantially all of the web structure can be inserted into an implant location (e.g., between two vertebra). Such a web structure and its micro-trusses can thus be employed to receive and distribute throughout the web structure loading forces of the surrounding tissue (e.g., vertebra, bone, or the like). In one embodiment, the diameters of the struts forming the micro-truss may be between about 0.25 millimeters (mm) and 5 mm in diameter (e.g., a diameter of about 0.25 mm, 0.5 mm, 0.6 mm, 0.7 mm, 0.8 mm, 0.9 mm, 1 mm, 2 mm, 3 mm, 4 mm, or 5 mm). In one embodiment, a micro-truss may have an overall length or width of less than about 1 inch (e.g., a length less than about 0.9 in, 0.8 in, 0.7 in, 0.6 in, 0.5 in, 0.4 in, 0.3 in, 0.2 in, 0.1 in).

As depicted, for example, in FIGS. 1A-1B, the web structure may extend throughout implant 100 (including the central portion of implant 100) to provide support throughout implant 100. Trusses 102 of implant 100 may thus support implant 100 against tensile, compressive, and shear forces. Web structure may also reinforce implant 100 along multiple planes. The external truss structure may, for example, provide support against tensile and compressive forces acting vertically through the implant, and the internal web structure may provide support against tensile, compressive, and shear forces along the various planes containing the respective trusses. In some embodiments, the web structure includes trusses 102 that form a triangulated web structure with multiple struts (e.g., struts 103*a-f*) (struts are generally referred to herein as "struts 103").

In one embodiment, web structure of the implant 100 may include an internal web structure that is at least partially enclosed by an external truss structure. For example, in one embodiment, web structure 101 may include an internal web structure that includes a space truss having at least a portion of the space truss surrounded by an external truss structure that includes one or more planar trusses formed with a plurality of planar truss units that lie substantially in a single plane. FIG. 1A depicts an embodiment of implant 100 having an internal web structure 104 and an external truss structure 105. In the illustrated embodiment, internal web structure 104 includes a space truss defined by a plurality of planar truss units 106 coupled at an angle with respect to one another such that each adjacent truss unit is not co-planar with each adjacent truss units. Adjacent truss units may include two truss units that share a strut and the respective two nodes at the ends of the shared strut.

In one embodiment, external truss structure 105 includes a plurality of planar trusses that are coupled about an exterior, interior or other portion of the implant. For example, in the illustrated embodiment, the external truss structure 105 includes a series of planar trusses 107*a,b* that are coupled to one another. Planar truss 107*a* is denoted by a dashed line [ - - - ], planar truss 107*b* is denoted by dotted-dashed line [ - - - ]. Each planar truss is formed from a plurality of planar truss units (e.g., triangular planar truss units. As depicted, planar truss 107*a* includes four triangular planar truss units 109*a,b,c,d* having a common vertex 110 and arranged to form a generally rectangular structure that lies in a single common plane. In other words, the four triangular planar truss units are arranged to form a substantially rectangular structure having "X" shaped struts extend from one corner of the rectangular structure to the opposite corner of the rectangular structure. As depicted, the substantially rectangular structure may include a trapezoidal shape. As described in more detail below, the trapezoidal shape may be conducive to providing an implant including lordosis. Lordosis may include an angled orientation of surfaces (e.g., top and bottom) of an implant that provides for differences in thickness in anterior and posterior regions of the implant such that the implant is conducive for supporting the curvature of a vertebral column.

In one embodiment, the planar trusses that form the external truss are coupled to one another, and are aligned along at least one axis. For example, in FIG. 1A, planar truss section 107a is coupled to an adjacent planar truss 107b. Planer truss sections 107a,b are not parallel in all directions. Planar truss sections 107a,b are, however, arranged parallel to one another in at least one direction (e.g., the vertical direction between the top and the bottom faces of implant 100). For example, planar trusses 107a,b and the additional planar trusses are arranged in series with an angle relative to one another to form a generally circular or polygon shaped enclosure having substantially vertical walls defined by the planar trusses and the planar truss units arranged in the vertical direction.

Figure 2A:
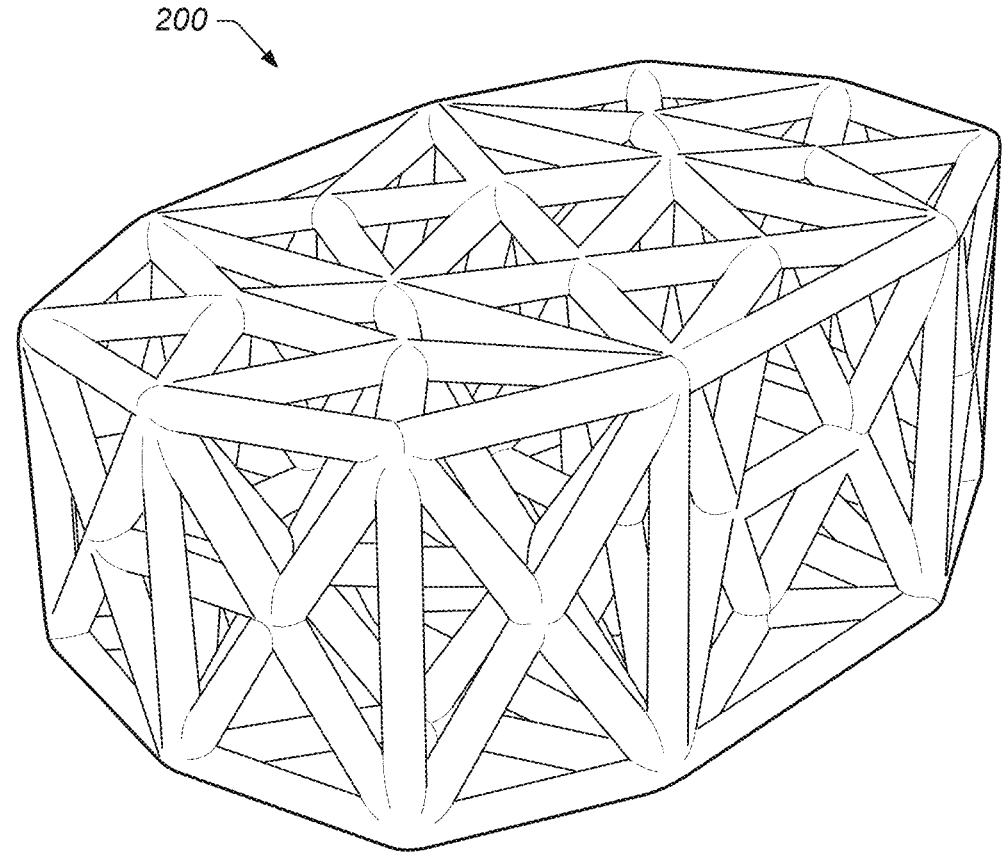
FIGS. 2A-2D illustrate views of an implant without lordosis, according to an embodiment.
Figure 2B:
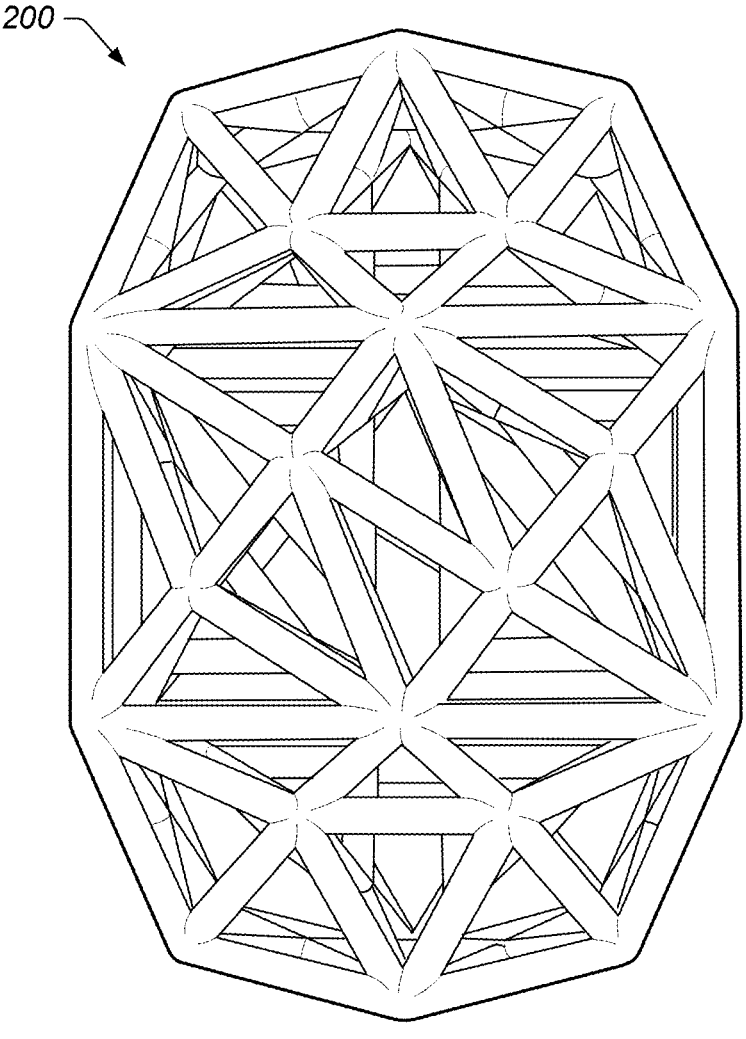
Figure 2C:
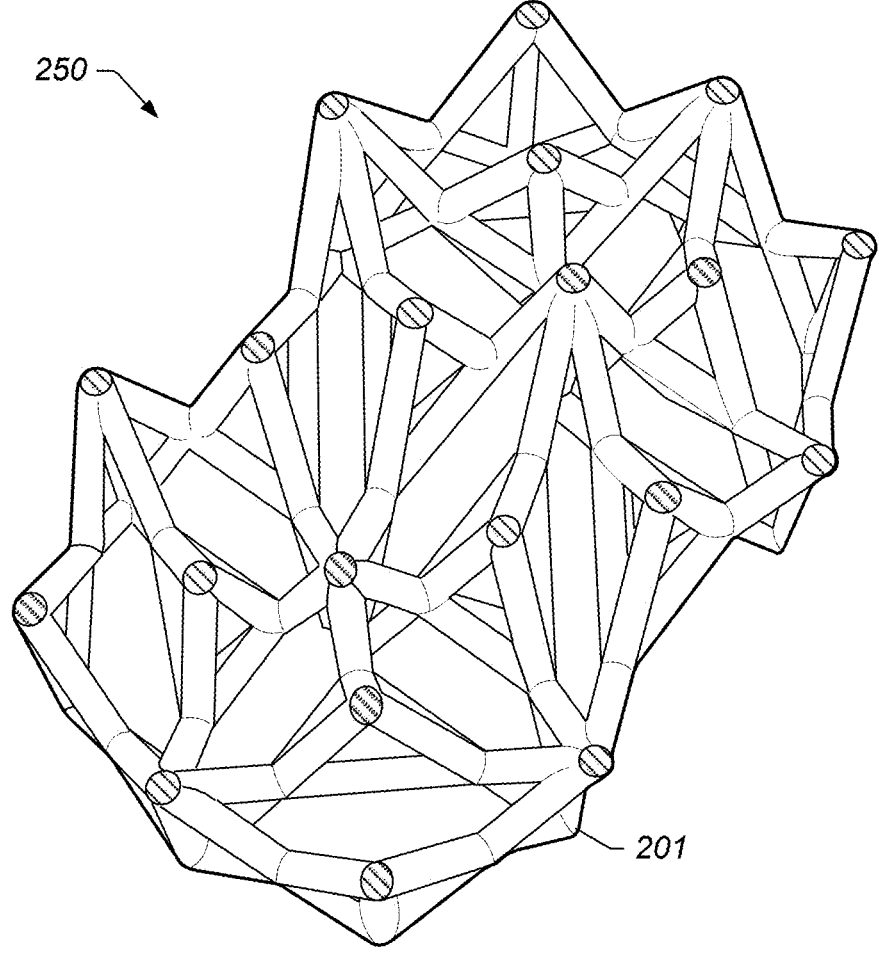

In one embodiment, the external truss portion may encompass the sides, top, and/or bottom of the implant. For example, in one embodiment, the external truss portion may include a top region, side regions, and/or a bottom region. FIG. 1A depicts an embodiment of implant 100 wherein external truss portion 105 includes a top 111, bottom 112 and a side region 113. As described above, side region 113 includes a series of planar trusses arranged vertically to form a circular/polygon ring-like structure that completely or at least partially surrounds the perimeter of the space truss disposed in the central portion of implant 100. In the depicted embodiment, top portion 111 of external truss structure 105 includes a plurality of truss units coupled to one another to form a planar truss that cover substantially all of the top region of internal web structure 104. In the illustrated embodiment, the top portion 111 spans entirely the region between top edges of the side portion 113 of external truss structure 105. In the illustrated embodiment, top portion 111 is formed from a single planar truss that includes a plurality of truss units that lie in substantially the same plane. In other words, the planar truss of top portion 111 defines a generally flat surface. Although difficult to view in FIG. 1, the underside of implant 100 may include the bottom portion 112 having a configuration similar to that of the top portion 111. In other embodiments, external truss structure 105 may include a partial side, top and/or bottom external truss portions. Or may not include one or more of the side, top and bottom external truss portions. For example, as described in more detail below, FIG. 2C depicts an embodiment of implant 100 that includes an internal web structure formed from space trusses, that does not have an external truss structure.

In some embodiments, implant 100 may be formed from a biocompatible material such as a titanium alloy (e.g., γTitanium Aluminides), cobalt, chromium, stainless steel, Polyetheretherketone (PEEK), ceramics, etc. Other materials are also contemplated. In some embodiments, implant 100 may be made through a rapid prototyping process (e.g., electron beam melting (EBM) process) as further described below. Other processes are also possible (e.g., injection molding, casting, sintering, selective laser sintering (SLS), Direct Metal Laser Sintering (DMLS), etc.). SLS may include laser-sintering of high-performance polymers such as that provided by EOS of North America, Inc., headquartered in Novi, Michigan, U.S.A. High-performance polymers may include various forms of PEEK (e.g., HP3 having a tensile strength of up to about 95 mega Pascal (MPa) and a Young's modulus of up to about 4400 MPa and continuous operating temperature between about 180° C. (356° F.) and 260° C. (500° F.)). Other materials may include PA 12 and PA 1I provided by EOS of North America, Inc.

Figure 7:
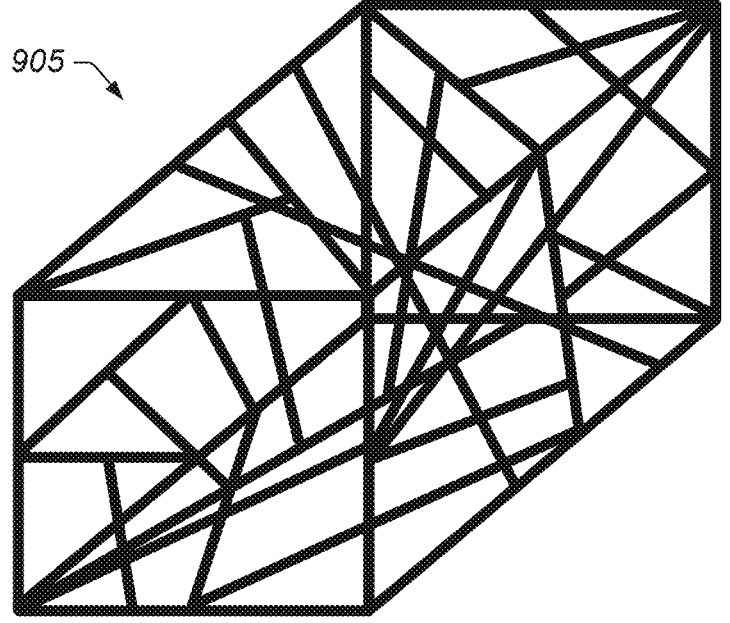
FIG. 7 illustrates a random web structure, according to an embodiment.

As described above, in some embodiments the web structure may be formed from a plurality of triangular planar truss units. In some embodiments, the planar truss units may be coupled to each other to define polyhedrons that define the internal web structure. Examples of polyhedron structures that may be created by joining planar truss units include, but are not limited to, tetrahedrons, pentahedrons, hexahedrons, heptahedrons, pyramids, octahedrons, dodecahedrons, icosahedrons, and spherical fullerenes. In some embodiments, such as those described above, the space truss of the web structure may connect multiple midpoints of tetrahedron building blocks and include a regular pattern of tetrahedron blocks arranged adjacent one another. In some embodiments, the web structure may not include a pattern of geometrical building blocks. For example, FIG. 7 illustrates an irregular pattern of struts that may be used in an implant 905. Other web structures are also contemplated. Examples of implants composed of a web structure are described in U.S. Published Patent Applications Nos.: 2010/0161061; 2011/0196495; 20110313532; and 2013/0030529, each of which is incorporated herein by reference.

Figure 3A:
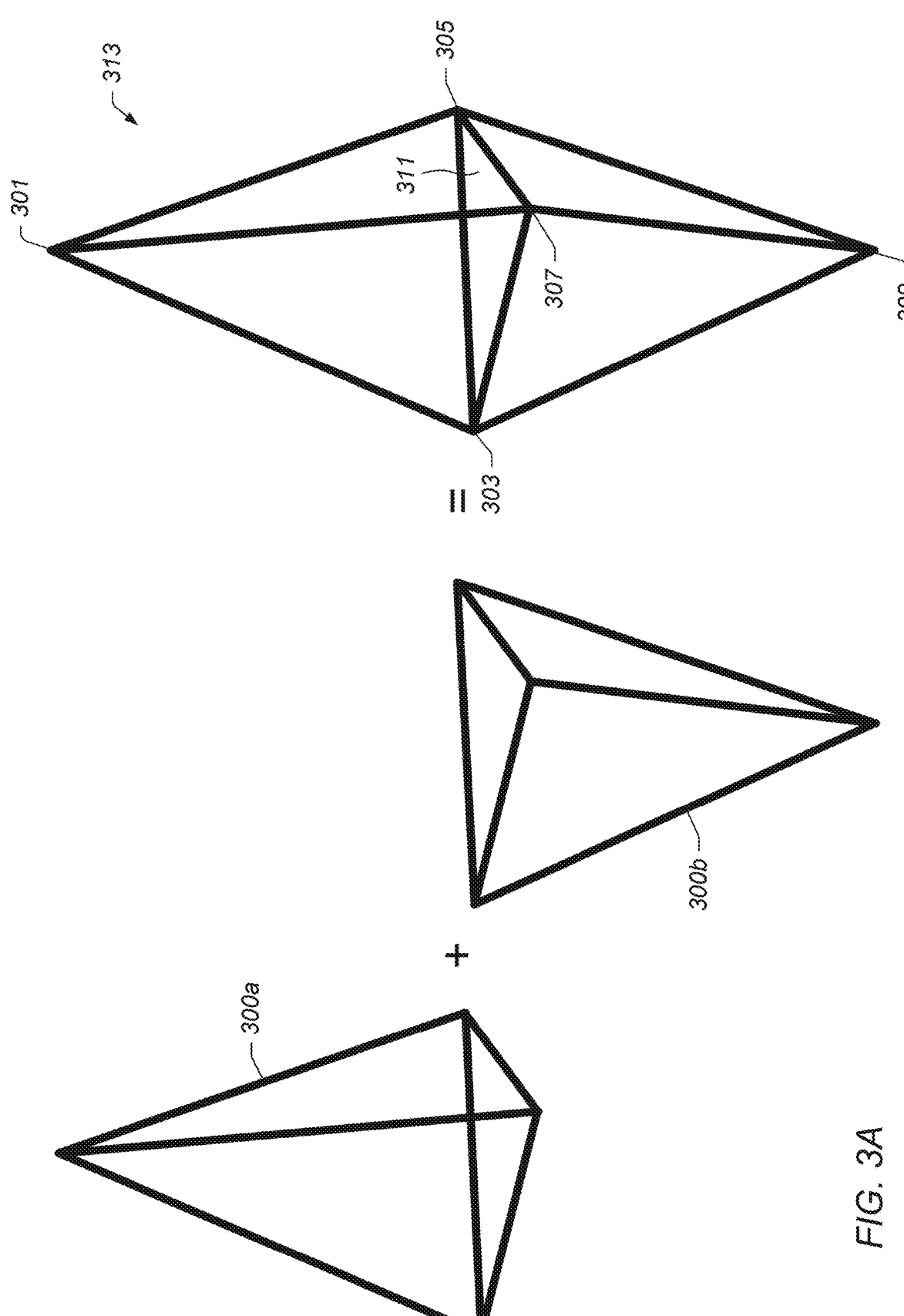
FIGS. 3A-3B illustrate a web structure formed with triangular-shaped building blocks, according to an embodiment.
Figure 3B:
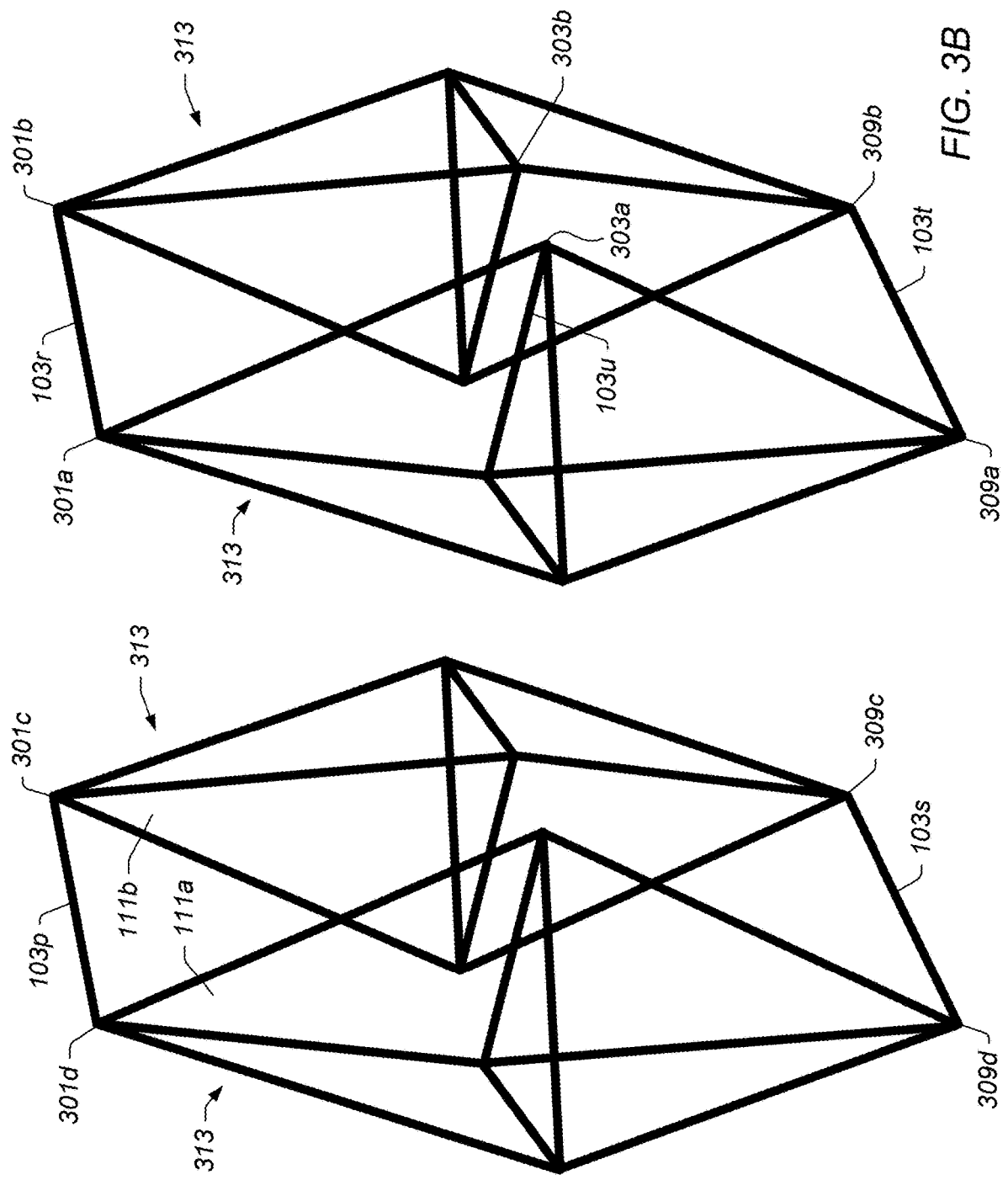

FIGS. 3A-3B illustrate a schematic view of a portion of an internal web structure formed with space units formed from triangular planar truss units. Triangular planar truss units may be joined together to form tetrahedrons 300a,b that may also be used as building blocks (other patterns from the triangles are also contemplated). Other building blocks are also contemplated (e.g., square-shaped building blocks). In some embodiments, a web structure may include a single tetrahedron, such as tetrahedron 300a or 300b alone or in combination with one or more other polyhedron. In some embodiments, a web structure may include two or more tetrahedrons 300a,b. Tetrahedron 300a may include four triangular faces in which three of the four triangles meet at each vertex. In some embodiments, two tetrahedrons 300a and 300b may be placed together at two adjacent faces to form space truss 313 with a hexahedron-shaped frame (including six faces). Hexahedron-shaped space truss 313 may include first vertex 301, second vertex 309, third vertex 303, fourth vertex 305, and fifth vertex 307. Common plane 311 may be shared by two tetrahedrons (e.g., common plane 311 may include third vertex 303, fourth vertex 305, and fifth vertex 307) to form a hexahedron with first vertex 301 and second vertex 309 spaced away from common plane 311. As depicted, the center portion of the triangular shaped building blocks may have a void region in their center that does not include any additional members (e.g., no members other than the struts forming the triangular shaped building blocks) extending there through.

As seen in FIG. 3B, in some embodiments, multiple hexahedron-shaped space trusses 313 may be arranged in a side-by-side manner. Two space trusses 313 of implant 100 may be connected via their first vertices 301a,b through strut 103r and connected via their second vertices 309a,b through strut 103t. Similarly, two space trusses 313 may be connected via their first vertices 301c,d through strut 103p and connected via their second vertices 309c,d through strut 103s. Other connections are also possible. For example, space trusses 313 may connect directly through side vertices (e.g., directly through corresponding vertices (such as vertices 303*ab*) and/or share a common strut (such as strut 103*u*)) and/or through a side face (e.g., side faces 111*a,b*).

Figures 4A, 4B:
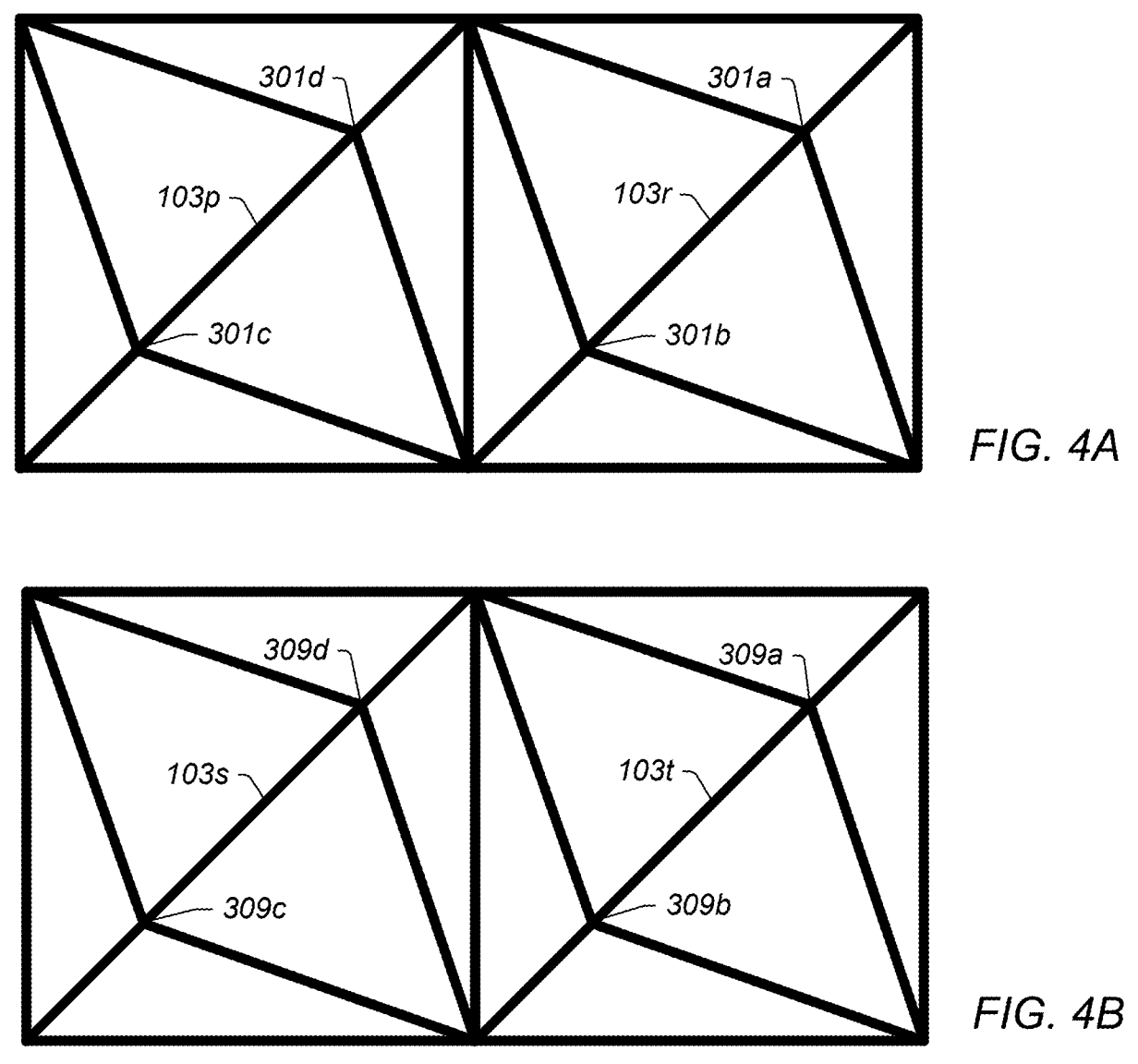

FIG. 4A illustrates additional struts 103 (e.g., struts 103*p* and 103*r*) connecting the first vertices (represented respectively by 301*a*, 301*b*, 301*c*, and 301*d*) of four hexahedron-shaped space trusses in implant 100. FIG. 4B illustrates additional struts 103 (e.g., struts 103*s* and 103*t*) connecting second vertices 309 (represented respectively by 309*a*, 309*b*, 309*c*, and 309*d*) of four hexahedron-shaped space trusses in implant 100. In some embodiments, additional struts 103 may also be used internally between one or more vertices of the web structures to form additional trusses (e.g., see web structures in FIGS. 1A-2B)(other structures are also possible).

As shown in FIG. 1A, top surface 115*a* and bottom surface 115*b* of implant 100 may include triangles, squares, circles or other shapes (e.g., a random or custom design). Top and bottom surfaces 115*a,b* may be used to connect the top and bottom vertices of various geometrical building blocks used in the web structure of implant 100. For example, each vertex may be connected through struts to the neighboring vertices of other geometrical building blocks. Top surface 115*a* may include other strut networks and/or connections. In some embodiments, bottom surface 115*b* may mirror the top surface (and/or have other designs). In some embodiments, top surface 115*a* and bottom surface 115*b* may engage respective surfaces of two adjacent vertebrae when implant 100 is implanted.

As depicted in FIG. 1B, implant 100 may include lordosis (e.g., an angle in top and/or bottom surfaces 115*a,b* approximately in a range of 4 to 15 degrees (such as 4, 5, 6, 7, 8, 9, 10, 11, 12, 13, 14, or 15 degrees)) to further support the adjacent vertebrae when implanted. As described above, lordosis may include an angled orientation of surfaces (e.g., top and bottom) that provide for differences in thickness in the anterior and posterior portions of the implant such that the implant is conducive for supporting the curvature of a vertebral column. In the illustrated embodiment, the thickness of implant 100 is greater at or near the anterior portion 118 and lesser at or near the posterior portion 120 of the implant. In the illustrated embodiment, the side portions of external truss structure are arranged substantially vertically, and the lordosis is formed by the angles of the top portion 111 and bottom portion 112 of external truss structure. For example, in the illustrated embodiment, top portion 111 and bottom portion 112 of external truss structure are not perpendicular to the vertical plane defined by the side portion 113. Rather, the top portion 111 and bottom portion 112 are arranged with an acute angle relative to the vertical plane of side portion 113 at or near the anterior region 118 of implant 100 and with an obtuse angle relative to the vertical plane of side portion 113 at or near posterior region 120 of implant 100. As depicted, the vertical struts that form the planar truss of side portion 113 of external truss structure proximate posterior region 120 of implant 100 are shorter than struts that form side portion of external truss structure proximate anterior region 118 of implant 100. In the illustrated embodiment, in which the vertical trusses are substantially evenly spaced, the struts forming the "X" cross members of the side planar trusses proximate the posterior region 120 of implant 100 are shorter than struts forming the "X" cross members of the side planar trusses proximate the anterior region 118 of implant 100. Other embodiments may include variations in the arrangement of the trusses to provide various configurations of the implant. For example, in some embodiments only one or neither of the top and bottom external truss portions may be non-perpendicular to the side portions of the external truss proximate the anterior and posterior portions of the implant. Further, the side, top, and/or bottom portions may include multiple planar trusses angled relative to one another in any orientation. For example, the top or bottom portions may include four planar trusses, each formed of multiple truss units, such that the portion(s) includes a pyramidal like shape.

Figure 2D:
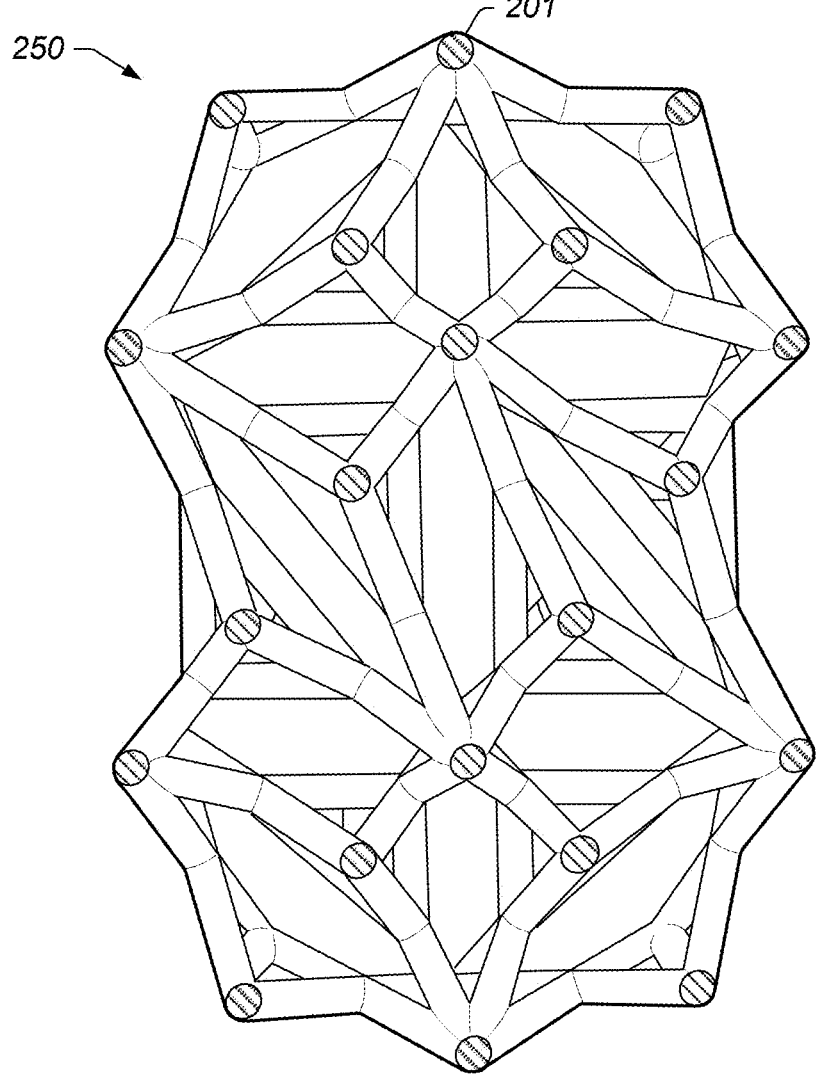

In some embodiments, the implant may not include lordosis. For example, FIGS. 2A-2B illustrate two views of an embodiment of an implant 200 without lordosis. In some embodiments, the top surface and bottom surface may not include connecting struts. For example, FIGS. 2C-2D illustrate two views of implant 250 without outer struts (e.g., without external truss portions formed of planar trusses). In the illustrated embodiment, implant 250 includes an internal web structure and does not include an external truss structure. For example, in the illustrated embodiment, the exterior faces of implant 250 are defined by a plurality of truss units that are angled relative to each of its adjacent truss units. The relative alignment of the truss units results in a non-planar exterior that includes a plurality of pointed junctions. The pointed junctions (e.g., pointed junction 201) may operate to dig into the surrounding bone to hold the implant in place (for example, if the implant is being used in a corpectomy device).

Figure 5A:
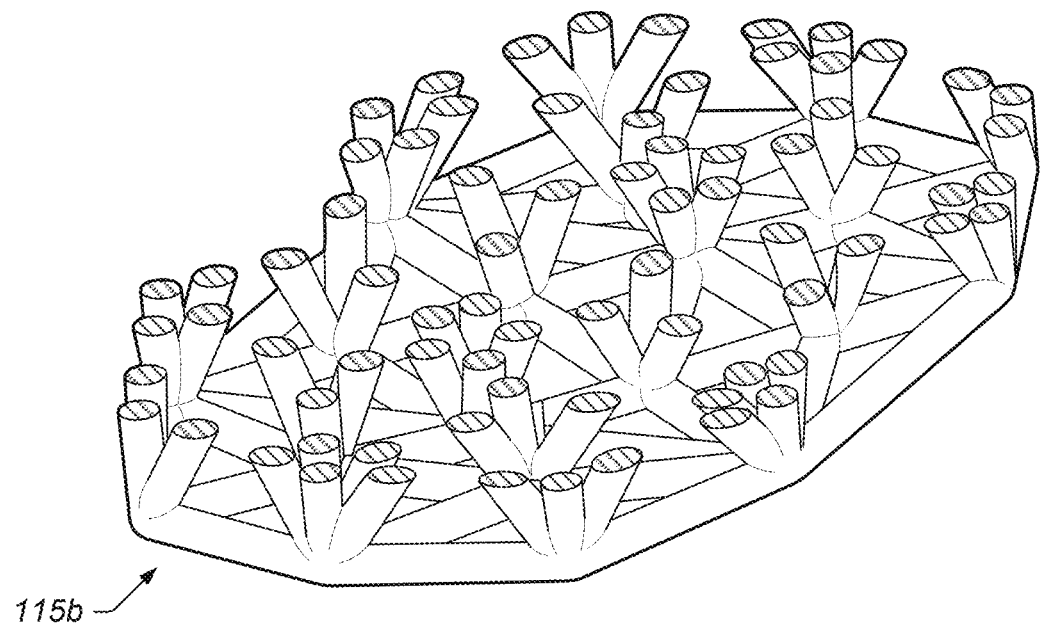
FIGS. 5A-5C illustrate progressive sectioned views of the implant showing the internal structure of the implant, according to an embodiment.
Figure 5B:
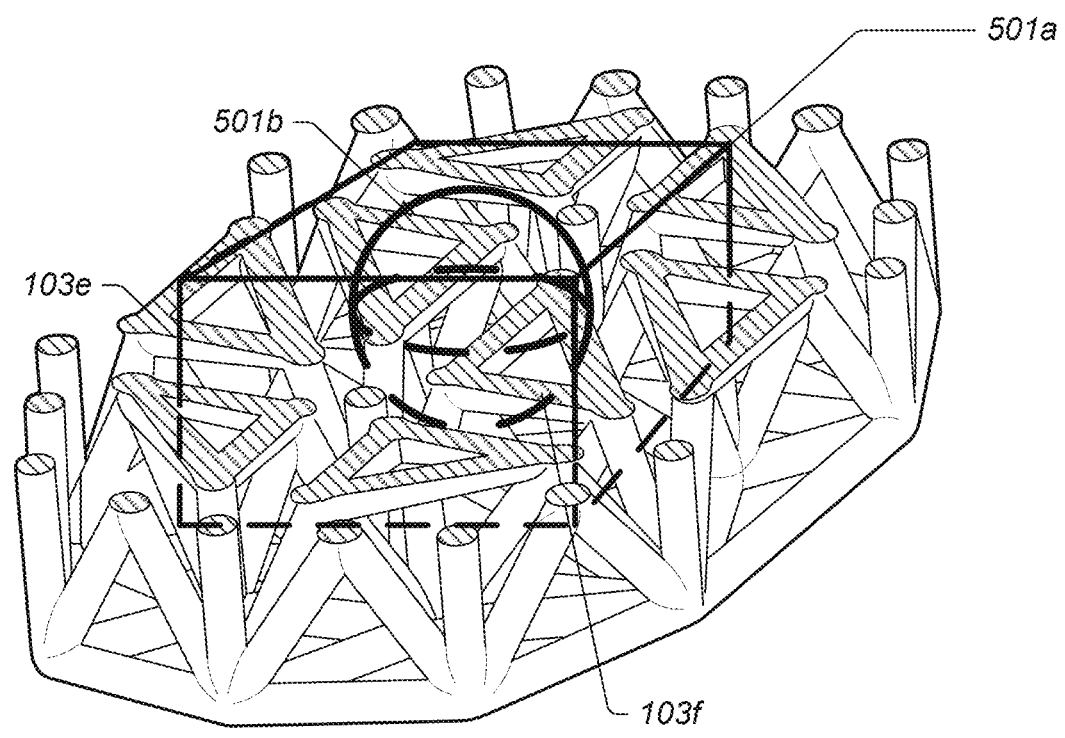
Figure 5C:
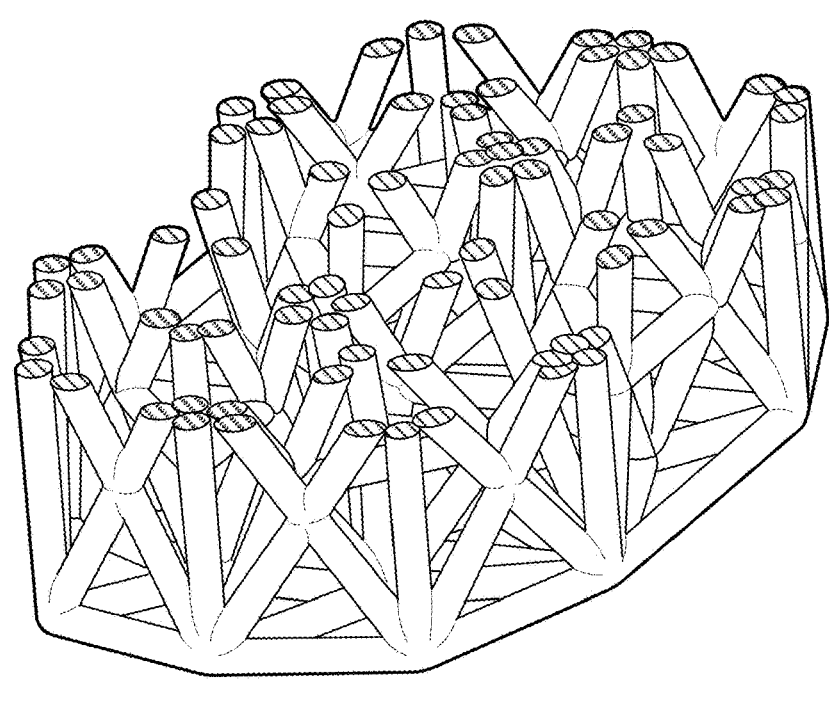
Figure 5D:
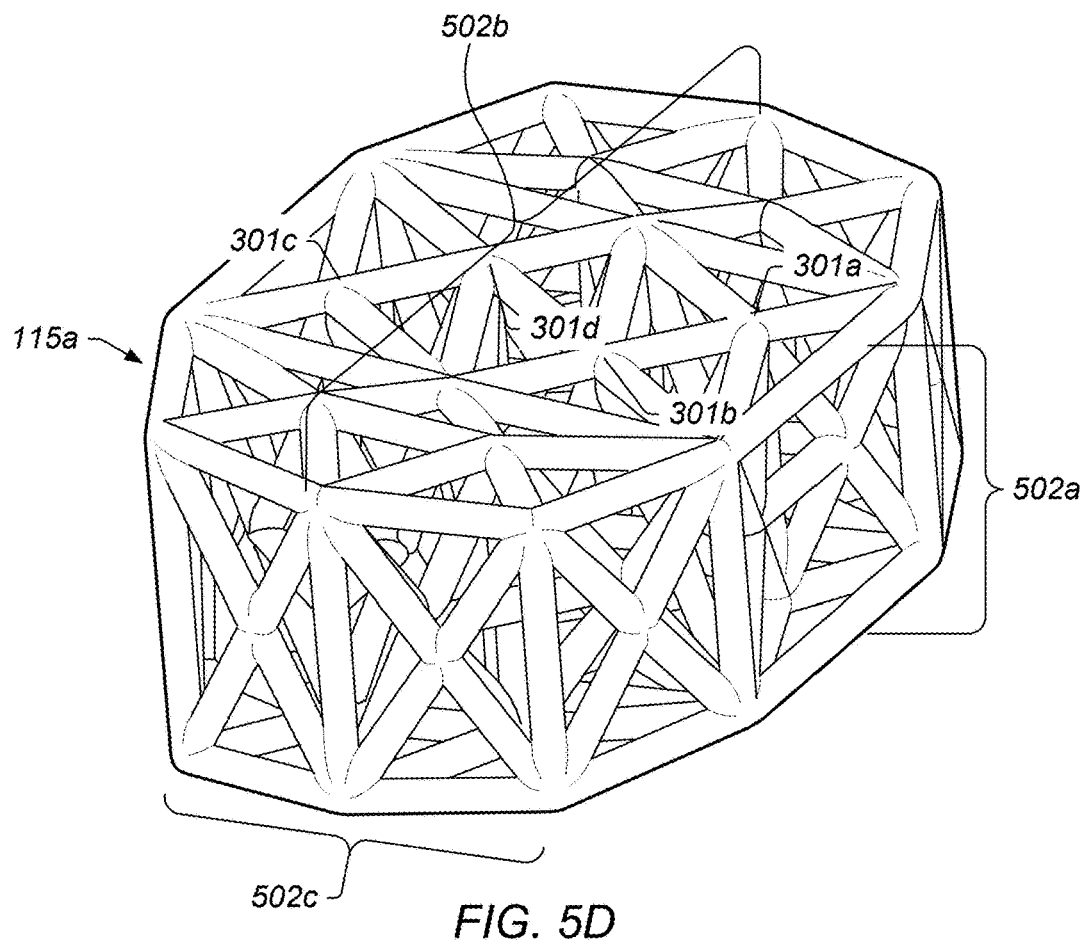
FIG. 5D illustrates an isometric view of the implant, according to an embodiment.

FIGS. 5A-5C illustrate progressive sectioned views of implant 100 showing the internal structure of implant 100, according to an embodiment. FIG. 5A illustrates a sectioned view of a lower portion of implant 100. Bottom surface 115*b* is shown with various struts (e.g., struts 103) extending upward from bottom surface 115*b*. FIG. 5B illustrates a sectioned view approximately mid-way through implant 100. Struts, such as struts 103*e,f*, shared by various stacked tetrahedrons in the web structure are shown. Some struts extend through central portion 501*a* and/or 501*b* of implant 100. FIG. 5B also shows central portions 51*a,b* of implant 100. In some embodiments, central portion 501*a* may include a rectangular region that has a width of approximately 50% of the implant width, a height of approximately 50% of the implant height, and a length of approximately 50% of the implant length and located in the center of implant 100. In some embodiments, central portion 501*b* may encompass a region (e.g., a spherical region, square region, etc.) of approximately a radius of approximately ⅛ to ¼ of the width of implant 100 around a position located approximately at one half the width, approximately one half the length, and approximately one-half the height of implant 100 (i.e., the center of implant 100). Other central portions are also contemplated. For example, the central portion may include a square region with a length of one of the sides of the square region approximately ⅛ to ½ the width of implant 100 around a position approximately at one half the width, approximately one half the length, and approximately one half the height of the implant. An example height 502*a*, width 502*b*, and length 502*c*, is shown in FIG. 5D. In some embodiments, the height may be up to about 75 mm or more. In some embodiments, such as those used for long bone reconstruction, the width and/or length could be approximately 7 inches or longer. In some embodiments, the width, length, and/or height may vary along implant 100 (e.g., the height may vary if the implant includes lordosis). The height may be taken at one of the opposing sides, the middle, and/or may be an average of one or more heights along the length of implant 100. The web structure may extend through central portion 501*a,b* of the implant (e.g., at least one strut of the web structure may pass at least partially through central portion 501*a,b*). FIG. 5C illustrates another sectioned view showing sectioned views of top tetrahedrons in the web structure. FIG. 5D shows a complete view of implant 100 including top surface 115*a* with vertices 301*a-d*.

Figure 6A:
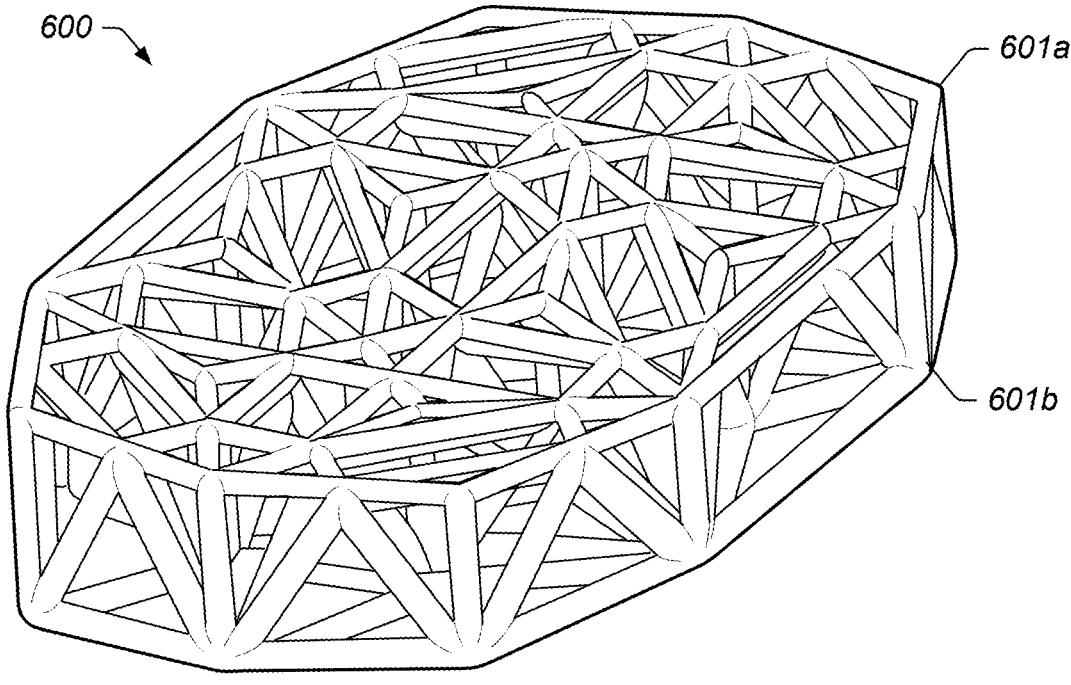
FIGS. 6A-6D illustrate another configuration of the web structure, according to an embodiment.
Figure 6B:
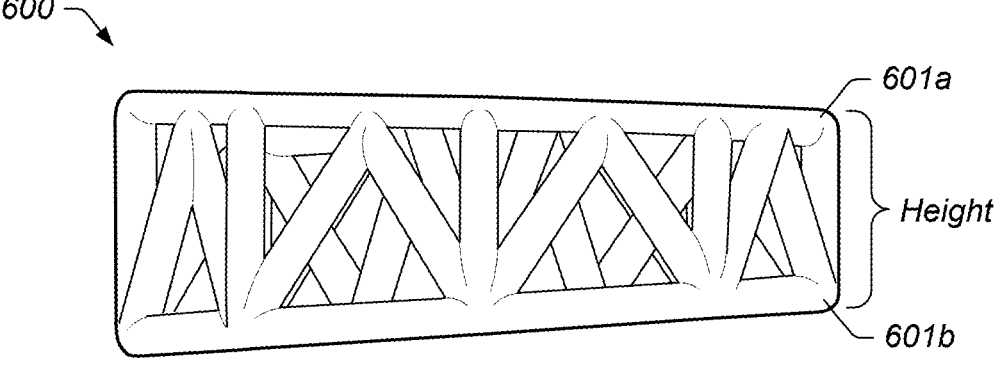

FIGS. 6A-6D illustrate alternate embodiments of an implant. In some embodiments, different sections of the hexahedron-shaped geometric design may be used. For example, as seen in FIG. 6A, the bottom half of the hexahedron-shaped geometric design may be used (primarily including the lower tetrahedron structures). If using the bottom half of the design, implant 600 may be expanded proportionately to have similar overall dimensions as the hexahedron-shaped geometric design (e.g., the tetrahedrons may be expanded to approximately twice the height of the tetrahedrons in the hexahedron-shaped geometric design to give implant 600 a height approximately the same as the hexahedron-shaped geometric design). In some embodiments, implant 600 may also be angled (e.g., on top surface 601*a* and/or bottom surface 601*b*) to provide implant 600 with lordosis to, in some embodiments, have a better fit between the vertebral endplates. Top surface 601*a* and/or bottom surface 601*b* may also include struts to connect nodes of implant 600 (e.g., see the strut network on the top surface in FIG. 6*a*). Other patterns of struts for top surface 601*a* and/or bottom surface 601*b* may also be used. In some embodiments, implant 600 may not include negative angles between struts and may thus be easier to create through a casting or molding process.

Figure 6C:
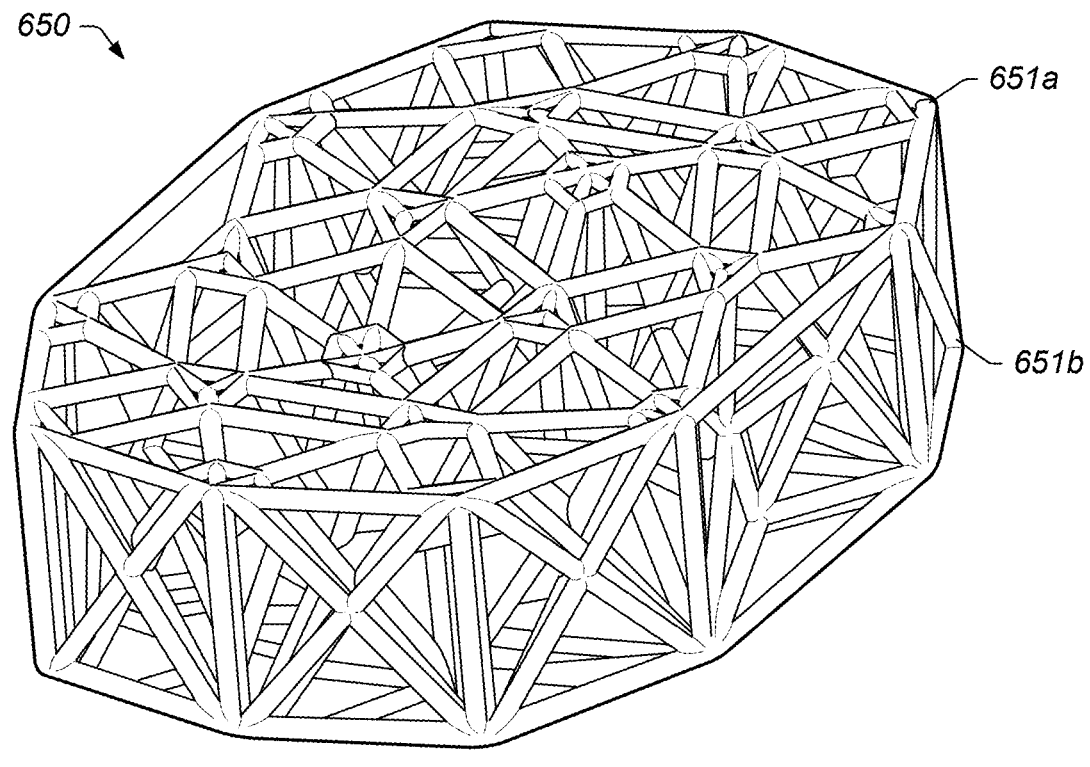
Figure 6D:
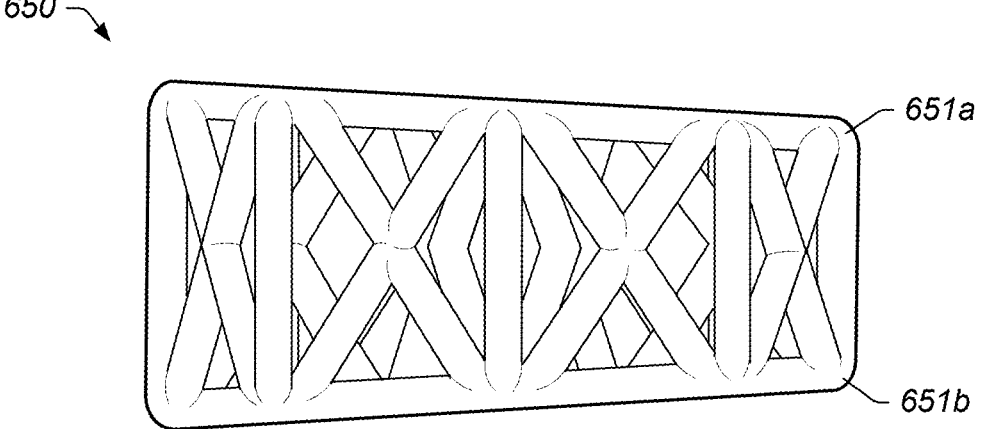

FIGS. 6C-6D illustrate another alternate embodiment of an implant. In some embodiments, approximately the middle 40 to 60 percent of the hexahedron-shaped geometric design may be used in implant 650. For example, if an overall height of the hexahedron-shaped geometric design is approximately 37 mm, approximately the bottom 10 mm and approximately the top 10 mm of the design may be removed and approximately the middle 17 mm of the design may be used for the implant. Middle portion of implant 650 may then be expanded proportionately such that the approximate height of the expanded design may be approximately 37 mm (or a different height as needed). Top surface 651*a* and bottom surface 651*b* may include a network of struts (e.g., see the struts on top surface 651*a* of FIG. 6C) (other networks of struts are also contemplated). Other portions of the design for the implant are also contemplated (e.g., the top half of the design shown in FIG. 1A, the bottom half of the design shown in FIG. 1A, etc.). Design portions may be proportionately expanded to meet specified dimensions (e.g., specified height, width, and length). In some embodiments, the amount of struts may be reduced or material in the implant may be redistributed so that some struts may have a larger diameter and some may have a smaller diameter (e.g., the different diameters may reinforce against different directional forces). In some embodiments, a partial-design cage may be used (e.g., with half of the web structure so that the structure includes a tetrahedron. Further, in some embodiments, the implant may include angled surfaces (e.g., an angled top surface 651*a* and/or angled bottom surface 651*b*) to provide lordosis for implants to be implanted between the vertebral endplates.

In some embodiments, the web structure of an implant may distribute forces throughout the implant when implanted. For example, the connecting struts of the web structure may extend throughout the core of an implant, and the interconnectivity of struts may disperse the stress of compressive forces throughout implant to reduce the potential of stress risers (the distribution of forces throughout the implant may prevent concentration of stress on one or more portions of the vertebrae that may otherwise result in damage to the vertebrae).

In some embodiments, the web structure of an implant (e.g., the external and internal struts of the implant) may also provide surface area for bone graft fusion. For example, the web structure extending throughout an implant may add additional surface areas (e.g., on the surface of the struts making up the implant) to fuse to the bone graft material and prevent bone graft material from loosening or migrating from the implant. In some embodiments, the web structure may also support bone in-growth. For example, when implanted, adjacent bone (e.g., adjacent vertebrae if the implant is used as a spinal implant) may grow over at least a portion of struts of the implant. The bone growth and engagement between the bone growth and the implant may further stabilize the implant. In some embodiments, the surfaces of the implant may be formed with a rough surface to assist in bone in-growth adhesion.

In some embodiments, struts may have a diameter approximately in a range of about 0.025 to 5 millimeters (mm) (e.g., 1.0 mm, 1.5 mm, 3 mm, etc.). Other diameters are also contemplated (e.g., greater than 5 mm). In some embodiments, the struts may have a length approximately in a range of 0.5 to 20 mm (e.g., depending on the implant size needed to, for example, fit a gap between vertebral endplates). As another example, struts may have a length approximately in a range of 30-40 mm for a hip implant. In some embodiments, the reduced strut size of the web structure may allow the open cells in implant 100 to facilitate bone growth (e.g., bone may grow through the open cells once implant 100 is implanted in the body). Average subsidence for implants may be approximately 1.5 mm within the first 3 weeks post op (other subsidence is also possible (e.g., approximately between 0.5 to 2.5 mm)). A strut size that approximately matches the subsidence (e.g., a strut size of approximately 1.5 mm in diameter and a subsidence of approximately 1.5 mm) may result in a net 0 impedance (e.g., the bone growth growing around the struts) after the implant has settled in the implanted position. The net 0 impedance throughout the entire surface area of the implant/vertebrae endplate interface may result in a larger fusion column of bone that may result in more stable fusion. Other fusion column sizes are also contemplated. The configuration of the implant may redistribute the metal throughout the implant. In some embodiments, a rim may not be included on the implant (in some embodiments, a rim may be included). The resulting bone growth (e.g., spinal column) may grow through the implant.

In some embodiments, greater than 50% of the interior volume of implant 100 may be open. In some embodiments, greater than 60%, greater than 70%, and/or greater than 80% of implant 100 may be open (e.g., 95%). In some embodiments, the open volume may be filled with bone growth material. For example, cancellous bone may be packed into an open/internal region of implant.

In some embodiments, at least a portion of the surfaces of the implant may be coated/treated with a material intend to promote bone growth and/or bone adhesion and/or an antimicrobial agent to prevent infections. For example, in some embodiments, the surface of the struts may be coated with a biologic and/or a bone growth factor. In some embodiments, a biologic may include a coating, such as hydroxyapatite, bone morphaginic protein (BMP), insulin-like growth factors I and II, transforming growth factor-beta, acidic and basic fibroblast growth factor, platelet-derived growth factor, and/or similar bone growth stimulant that facilitates good biological fixation between the bone growth and a surface of the implant. In some embodiments, a bone growth factor may include a naturally occurring substance capable of stimulating cellular growth, proliferation and cellular differentiation (e.g., a protein or steroid hormone). In some embodiments, the surface of the implant (e.g., the struts, the external truss structure, etc.) may be coated with collagen.

In some embodiments, a biologic and/or growth factor may be secured to a central region of an implant. For example, in some embodiments, a biologic or growth factor may be provided on at least a portion of a strut that extends through central portion 501*a* and/or 51*b* of implant 100, see FIG. 5B. Such an embodiment may enable the delivery of a biologic and or a growth factor to a central portion of an implant. For example, the biologic or growth factor may be physically secured to a strut in a central portion of the implant as opposed to being packed into an open volume that does not include a strut provided therein for the physical attachment of the biologic and/or growth factor.

As the implant settles into the implant site, subsidence may place additional pressure on the bone graft material (which may already be under compressive forces in the implant) and act to push the bone graft material toward the sides of the implant (according to Boussinesq's theory of adjacent material, when a force is applied to a member that is adjacent to other materials (such as sand, dirt, or bone graft material) the force against the member creates a zone of increased pressure (e.g., 60 degrees) in the adjacent material). Struts of the implant may resist bone graft material protrusion from the sides of the web structure and may increase the pressure of the bone graft material. Bone graft material may need to be implanted in a higher-pressure environment to create an environment conducive to strong bone growth (e.g., according to Wolf's law that bone in a healthy person or animal will adapt to the loads it is placed under). The web structure may thus increase the chance of stronger fusion.

Web structures formed from other truss configurations are also contemplated. For example, the trusses may include a series of packing triangles, a two-web truss, a three-web truss, etc. Further, the web structure for an implant may include one or more trusses as described in U.S. Pat. No. 6,931,812 titled "Web Structure and Method For Making the Same", which issued Aug. 23, 2005, which is hereby incorporated by reference in its entirety as though fully and completely set forth herein.

Figure 8:
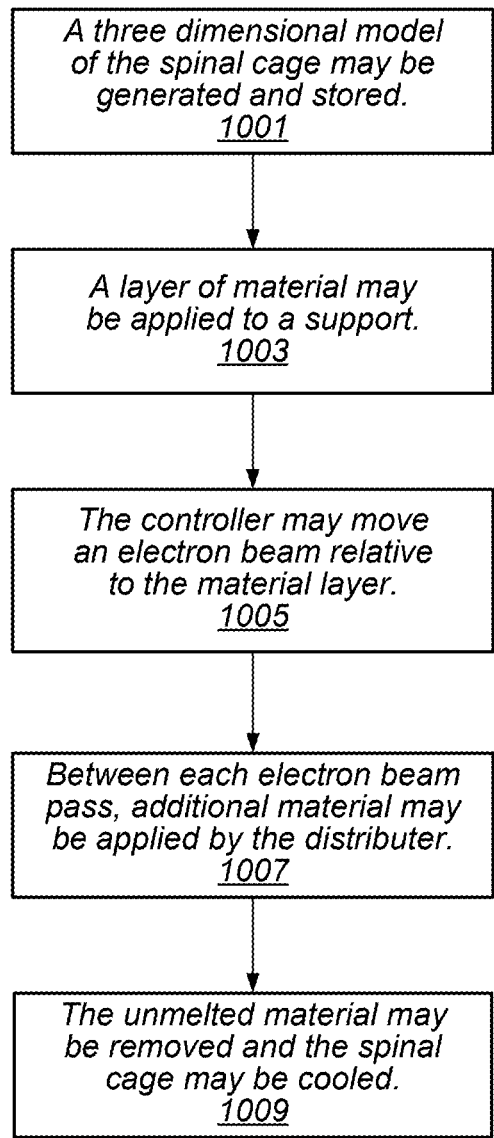
FIG. 8 illustrates a flowchart of a method for making an implant, according to an embodiment.

FIG. 8 illustrates a flowchart of a method for making an implant. In some embodiments, an implant may be made through rapid prototyping (e.g., electron beam melting, laser sintering, etc.). It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At 1001, a three dimensional model of an implant is generated and stored in a storage medium accessible to a controller operable to control the implant production process. At 1003, a layer of material (e.g., a powder, liquid, etc.) is applied to a support. In some embodiments, the powder may include γTiAl (γTitanium Aluminides) which may be a high strength/low weight material. Other materials may also be used. The powder may be formed using a gas atomization process and may include granules with diameters approximately in a range of 20 to 200 micrometers (μm) (e.g., approximately 80 μm). The powder may be delivered to the support through a distributer (e.g., delivered from a storage container). The distributer and/or the support may move during distribution to apply a layer (e.g., of powder) to the support. In some embodiments, the layer may be approximately a uniform thickness (e.g., with an average thickness of 20 to 200 micrometers (μm)). In some embodiments, the distributer and support may not move (e.g., the material may be sprayed onto the support). At 1005, the controller moves an electron beam relative to the material layer. In some embodiments, the electron beam generator may be moved, and in some embodiments the support may be moved. If the material is γTiAl, a melting temperature approximately in a range of 1200 to 1800 degrees Celsius (e.g., 1500 degrees Celsius) may be obtained between the electron beam and the material. At 1007, between each electron beam pass, additional material may be applied by the distributer. At 1009, the unmelted material is removed and the implant cooled (e.g., using a cool inert gas). In some embodiments, the edges of the implant may be smoothed to remove rough edges (e.g., using a diamond sander). In some embodiments, the implant may include rough edges to increase friction between the implant and the surrounding bone to increase adhesion of the implant to the bone.

Other methods of making an implant are also contemplated. For example, an implant may be cast or injection molded. In some embodiments, multiple parts may be cast or injection molded and joined together (e.g., through welding, melting, etc.). In some embodiments, individual struts forming the implant may be generated separately (e.g., by casting, injection molding, etc.) and welded together to form the implant. In some embodiments, multiple implants of different sizes may be constructed and delivered in a kit. A medical health professional may choose an implant (e.g., according to a needed size) during the surgery. In some embodiments, multiple implants may be used at the implant site.

Specialized tools may be used to insert the implants described herein. Examples of tools that may be used are described in U.S. Published Patent Applications Nos.: 2010/0161061; 2011/0196495; 20110313532; and 2013/0030529, each of which is incorporated herein by reference.

Figure 9:
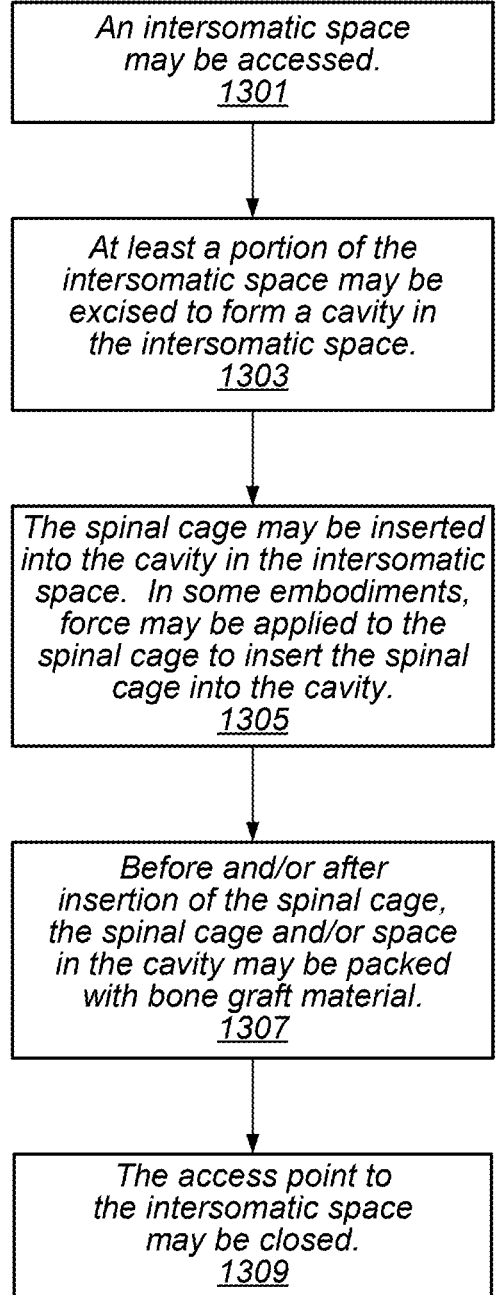
FIG. 9 illustrates a flowchart of a method for implanting a spinal implant, according to an embodiment.

FIG. 9 illustrates a flowchart of a method for implanting a spinal implant, according to an embodiment. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

At step 1301, an intersomatic space is accessed. For example, an anterior opening may be made in a patient's body for an anterior lumbar inter-body fusion (ALIF) approach or a posterior opening may be made for a posterior lumbar inter-body fusion (PLIF) approach. At 1303, at least a portion of the intersomatic space is excised to form a cavity in the intersomatic space. At 1305, the implant is inserted into the cavity in the intersomatic space. In some embodiments, a handler, or some other device, is used to grip the implant. In some embodiments, a force may be applied to the implant (e.g., through a hammer) to insert the implant into the cavity. At 1307, before and/or after insertion of the implant, the implant and/or space in the cavity may be packed with bone graft material. At 1309, the access point to the intersomatic space may be closed (e.g., using sutures).

In some embodiments, the implant may be customized. For example, three dimensional measurements and/or shape of the implant may be used to construct an implant that distributes the web structure throughout a three-dimensional shape design.

In some embodiments, a truss/web structure may be disposed on at least a portion of an implant to facilitate coupling of the implant to an adjacent structure. For example, where an implant is implanted adjacent a bony structure, one or more truss structures may be disposed on and/or extend from a surface (e.g., an interface plate) of the implant that is intended to contact, and at least partially adhere to, the bony structure during use. In some embodiments, such as those including an intervertebral implant disposed between the end plates of two adjacent vertebrae during, one or more truss structures may be disposed on a contact surface of the intervertebral implant to facilitate bone growth that enhances coupling of the intervertebral implant to the bony structure. For example, a truss structure may include one or more struts that extend from the contact surface to define an open space for bone growth therethrough, thereby enabling bone through growth to interlock the bone structure and the truss structure with one another to couple the implant to the bony structure at or near the contact face. Such interlocking bone through growth may inhibit movement between the implant and the bony structure which could otherwise lead to loosening, migration, subsidence, or dislodging of the implant from the intended position. Similar techniques may be employed with various types of implants, including those intended to interface with tissue and/or bone structures. For example, a truss structure may be employed on a contact surface of knee implants, in a corpectomy device, in a hip replacement, in a knee replacement, in a long bone reconstruction scaffold, or in a cranio-maxifacial implant hip implants, jaw implant, an implant for long bone reconstruction, foot and ankle implants, shoulder implants or other joint replacement implants or the like to enhance adherence of the implant to the adjacent bony structure or tissue. Examples of truss structures, and other structures, that may extend from the surface of an implant to facilitate coupling of the implant to an adjacent structure are described in U.S. Published Patent Application No. 2011/0313532, which is incorporated herein by reference.

While implants described herein are depicted as being composed of substantially straight struts, it should be understood that the struts can be non-linear, including, but not limited to curved, arcuate and arch shaped. Examples of implants having non-linear struts are described in U.S. patent application Ser. No. 13/668,968, which is incorporated herein by reference.

Figure 10A:
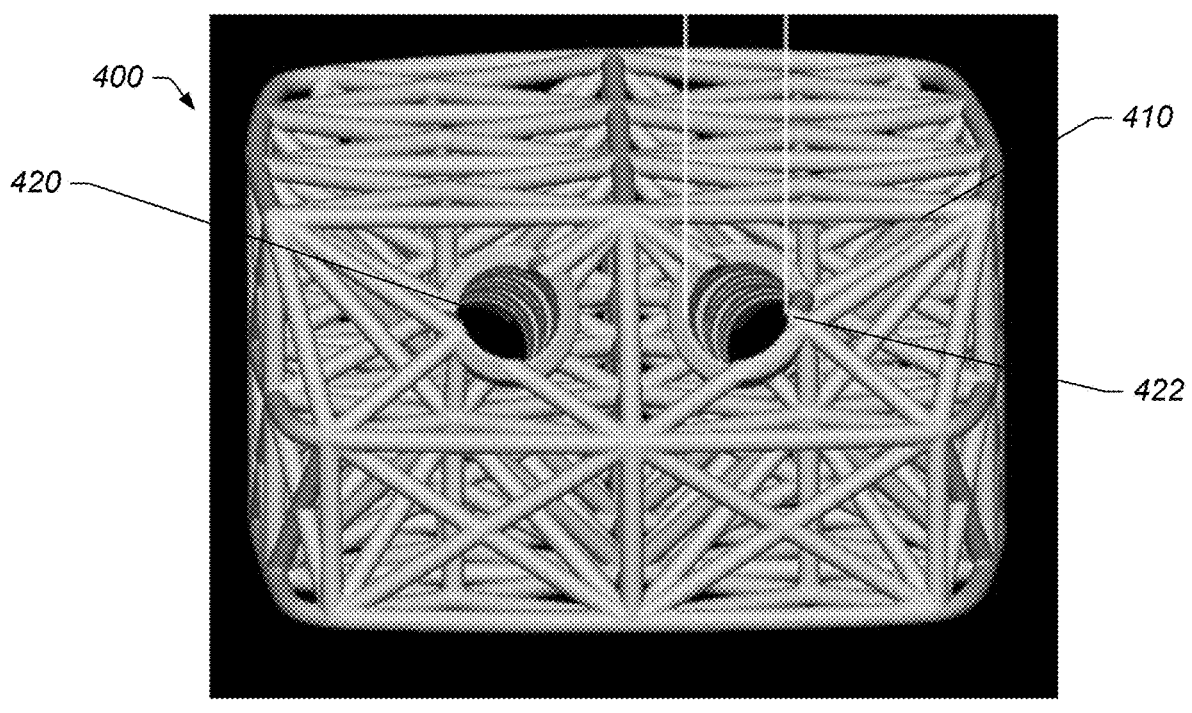
FIGS. 10A-C depict an implant having one or more channels extending through the implant.
Figure 10B:
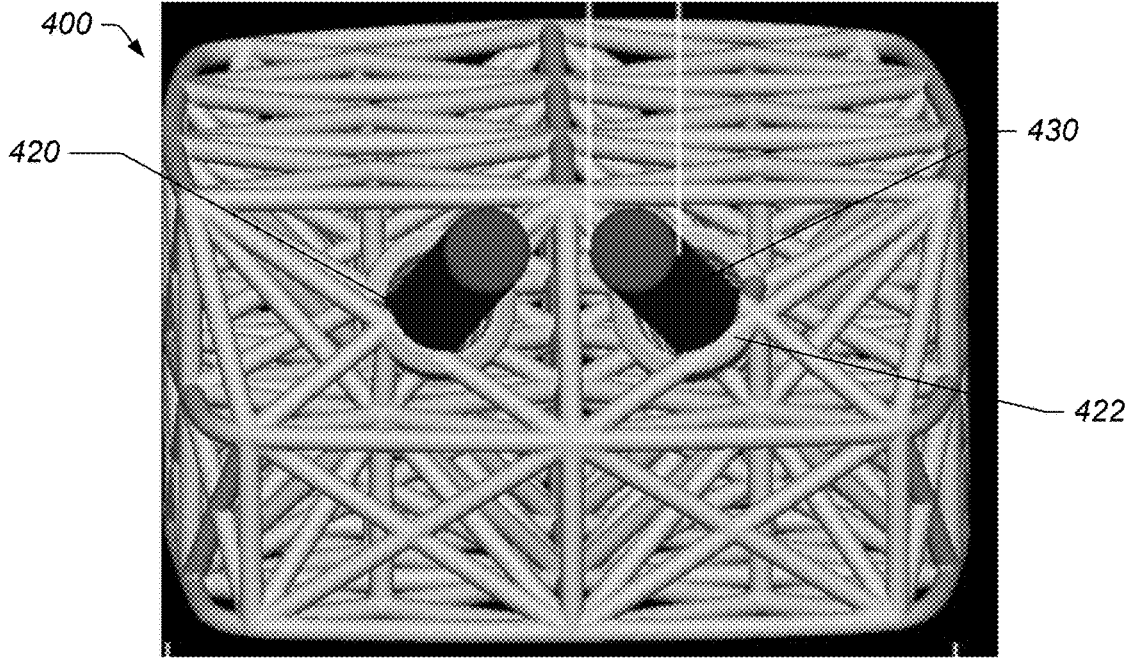
Figure 10C:
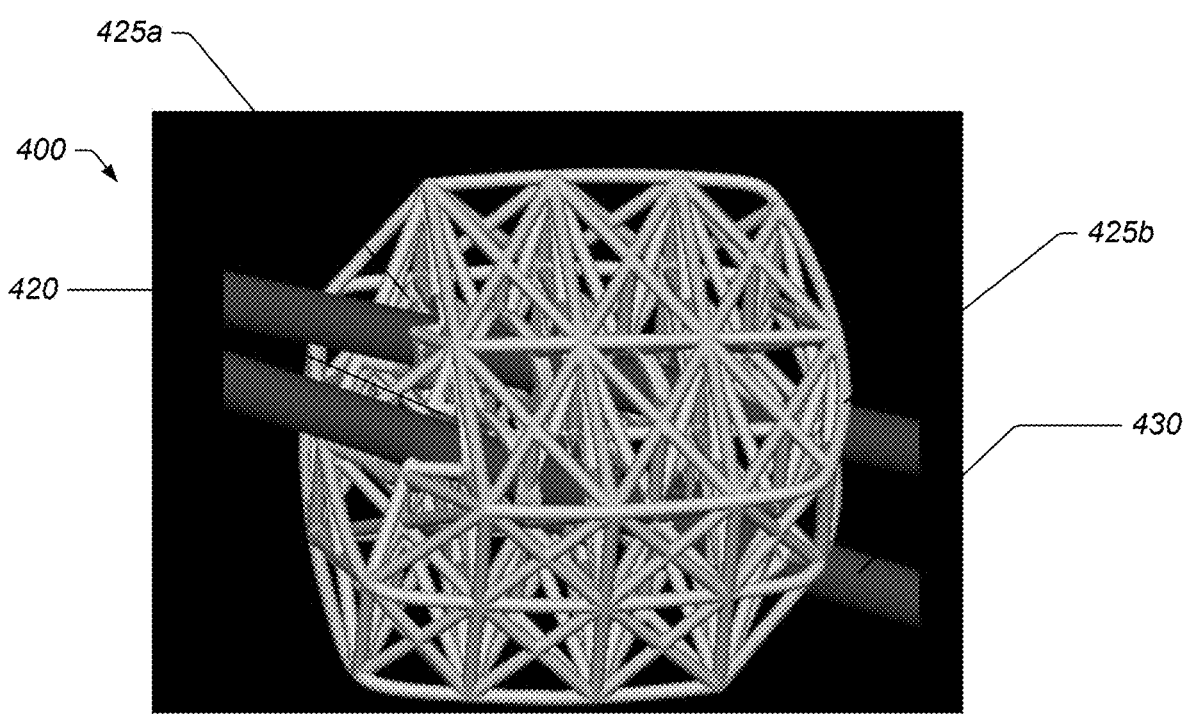

In some embodiments, it is desirable for an implant to be secured to the bone using one or more fasteners (e.g., screws). Fasteners may be coupled to any part of the implant structure to secure the implant to the bone. An embodiment of an implant having one or more channels that can receive a fastener is depicted in FIGS. 10A, 10B, and 10C. In one embodiment, implant 400 is composed of a web structure that includes a space truss 410 formed from two or more planar truss units having a plurality of struts joined at nodes. One or more channels 420 are formed in the web structure. The channels extend through the web structure such that channel exits 425a,b are present in at least two sides of the web structure (See FIG. 10C). Channels may be defined by one or more substantially arcuate and/or circular struts 422 coupled to one or more adjacent planar truss units.

The channels may be substantially tubular to receive a cylindrical fastener 430 (e.g., a bone screw). Fastener 430 may move within channel 420 such that the sides of the fastener are not attached to space truss 410. In such embodiments, fastener 430 may include a head (not shown) which contacts a surface of implant 400 to secure the implant to the bone. Alternatively, channels 420 may be substantially threaded, having a threading that is complementary to threading of a bone screw. During use, a bone screw is coupled to channel 420 by mating the bone screw with the threading of the channel. The threading of channel 420, when coupled to the bone screw, help prevent pull out of the fastener from the implant.

Figure 11:
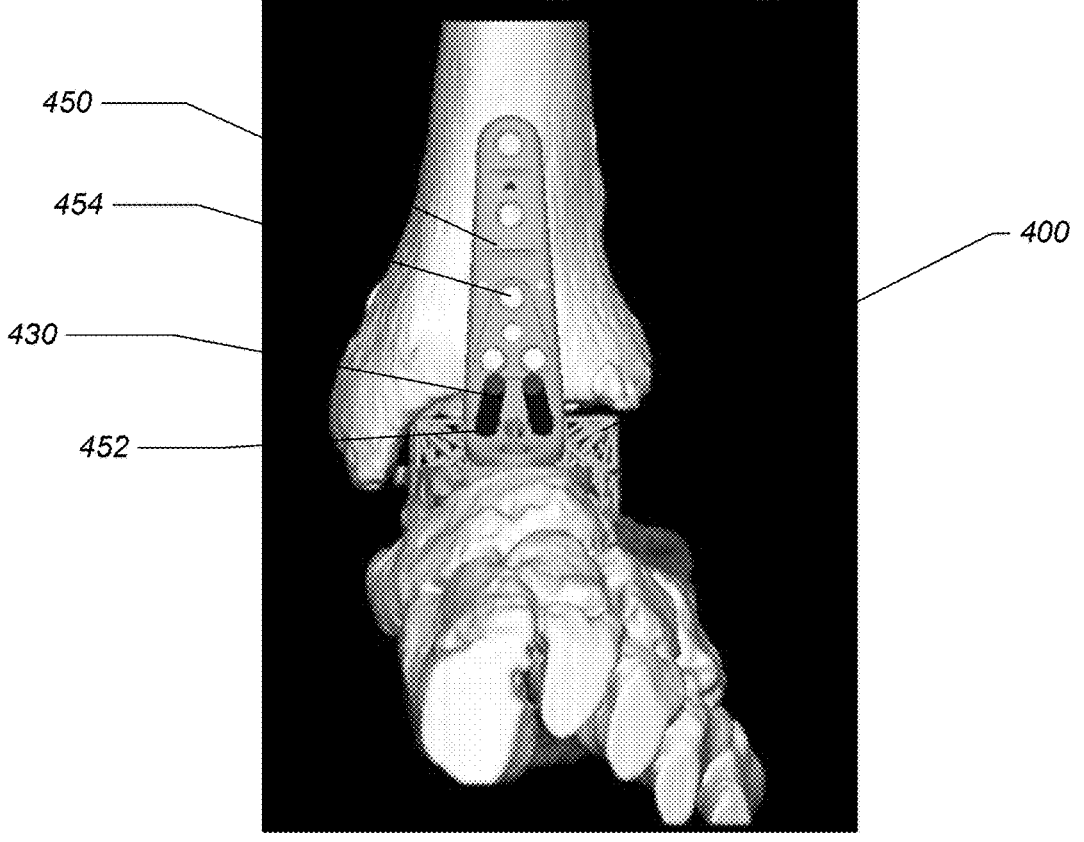

An external support 450 may also be used to secure implant 400 to a bone structure, as depicted in FIG. 11. External support 450 may be coupled to the web structure of implant 400 using one or more fasteners 430. Fasteners 430, therefore, may pass through external support 450, into channels 420 and into a bone structure to secure implant 400 and the external support to the bone. External support 450 may include one or more openings 452 that correspond to the position of channels 420 disposed in implant 400. External support 450 may include additional openings 454, which allow the support to be independently coupled to a bone structure. While depicted as a separate component of the implant system, it should be understood that external support may be integrated with implant 400 to form a unitary implant that includes a space truss attached to an external support.

In one embodiment, a bone structure may be repaired using implant 400. The implant 400 may be placed proximate to, or in contact with, a bone structure in need of repair. Fasteners 430 may be positioned in one or more of channels 420 and coupled to the bone structure. In some embodiments, fasteners 430 are bone screws. A bone screw may be inserted into channels 420 and fastened to the bone by screwing the bone screw into the bone structure. In some embodiments, channels 420 may have threading complementary to the bone screw threading, such that the bone screw is coupled to the implant as well as the bone structure.

In some embodiments, an external support 450 may be used to secure the implant to the bone structure. Implant 400 may be placed proximate to a bone structure. External support 450 may be placed proximate to, or in contact with, implant 400, such that at least some of the openings 452 on external support 450 are aligned with one or more channels 420 of the implant. Fasteners (e.g., bone screws) may be positioned through openings 452 into channels 420, and coupled to the underlying bone structure. Additional fasteners may be positioned in one or more additional openings 454 and coupled to an external portion of the bone structure to provide additional support to the implant.

In an alternate method, external structure 450 may be used as a guide for forming channels in an implant that does not have channels. An implant, such as implant 100, may be positioned proximate to, or in contact with, a bone structure in need of repair. External support 450 may be placed proximate to, or in contact with, a bone structure and implant 100. At least a portion of the openings 452 of external structure 450 are aligned with a portion of the implant. A drill, or other cutting device, may be used to form channels in the implant, using the external support as a guide to determine where the channels are formed. The openings of the external support used to form the channels have a depth sufficient to control the angle that the channel is drilled by providing a guide for the drill bit. The channels of the implant may be custom made during implantation by selecting the external support having openings that will produce channels at the desired location and angle.

In an embodiment, an implant 700 includes a distal end 720 and a proximal end 710, wherein the proximal end comprises a space truss 715 comprising two or more planar truss units having a plurality of struts joined at nodes. The space truss is configured to interface with human bone tissue. Distal end 720 includes threading 725 which allows the implant to be screwed into a bone structure. In some embodiments the threaded distal end is substantially solid. The threaded distal end, in some embodiments, is a space truss having exterior threading. Slot 730 may be used to insert the bone screw into a bone structure.

Figure 12:
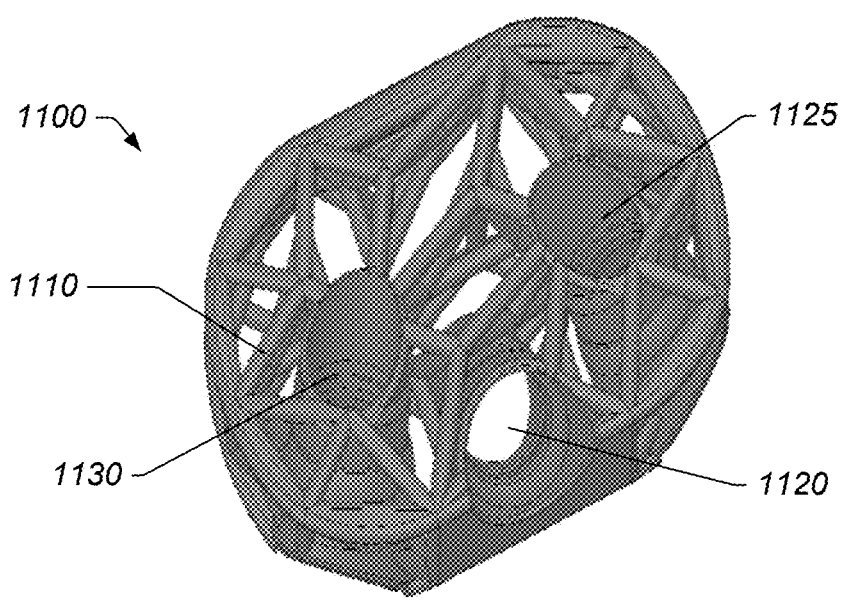
FIG. 12 depicts an embodiment of an implant having three channels.

FIG. 12 depicts an embodiment of an implant having one or more channels that can receive a fastener. In one embodiment, implant 1100 is composed of a web structure that includes a space truss 1110 formed from two or more planar truss units having a plurality of struts joined at nodes. One or more channels 1120 are formed in the web structure. The channels extend through the web structure such that channel exits are present in at least two sides of the web structure. Channels may be defined by a channel structure 1125 coupled to one or more adjacent planar truss units.

The channels may be substantially tubular to receive a cylindrical fastener (e.g., a bone screw). A fastener may move within channel 1120 such that the sides of the fastener are not attached to space truss 1110. In such embodiments, a fastener may include a head (not shown) which contacts a surface of implant 1100 to secure the implant to the bone. Alternatively, channel structures 1125 may include threading 1130 that is complementary to threading of a bone screw. During use, a bone screw is coupled to channel 1120 by mating the bone screw with the threading of the channel. The threading of channel 1120, when coupled to the bone screw, help prevent pull out of the fastener from the implant.

Figure 13:
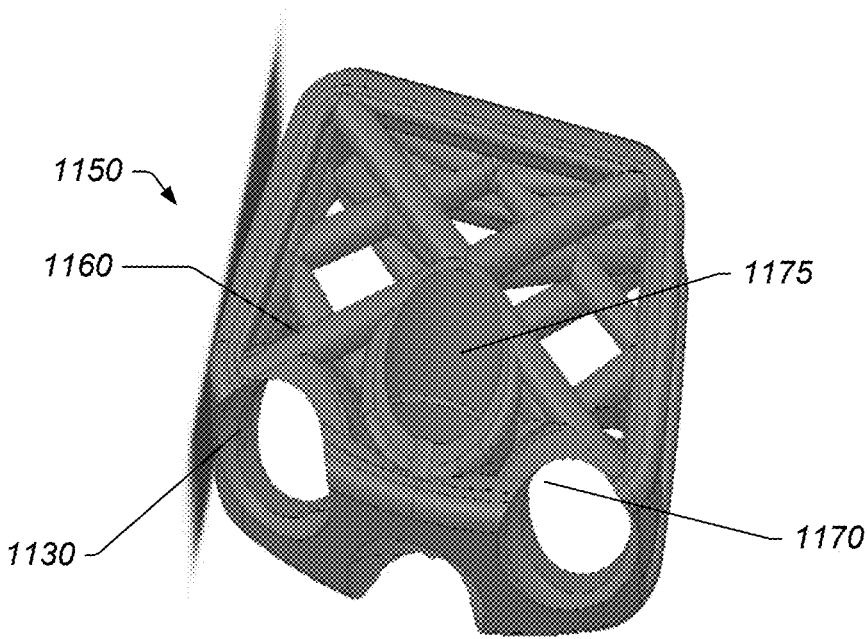
FIG. 13 depicts an alternate embodiment of an implant having three channels.

FIG. 13 depicts an embodiment of an implant having one or more channels that can receive a fastener. In one embodiment, implant 1150 is composed of a web structure that includes a space truss 1160 formed from two or more planar truss units having a plurality of struts joined at nodes. One or more channels 1170 are formed in the web structure. The channels extend through the web structure such that channel exits are present in at least two sides of the web structure. Channels may be defined by a channel structure 1175 coupled to one or more adjacent planar truss units.

The channels may be substantially tubular to receive a cylindrical fastener (e.g., a bone screw). A fastener may move within channel 1170 such that the sides of the fastener are not attached to space truss 1160. In such embodiments, a fastener may include a head (not shown) which contacts a surface of implant 1150 to secure the implant to the bone. Alternatively, channel structures 1175 may include threading 1180 that is complementary to threading of a bone screw. During use, a bone screw is coupled to channel 1170 by mating the bone screw with the threading of the channel. The threading of channel 1170, when coupled to the bone screw, help prevent pull out of the fastener from the implant.

Figure 14:
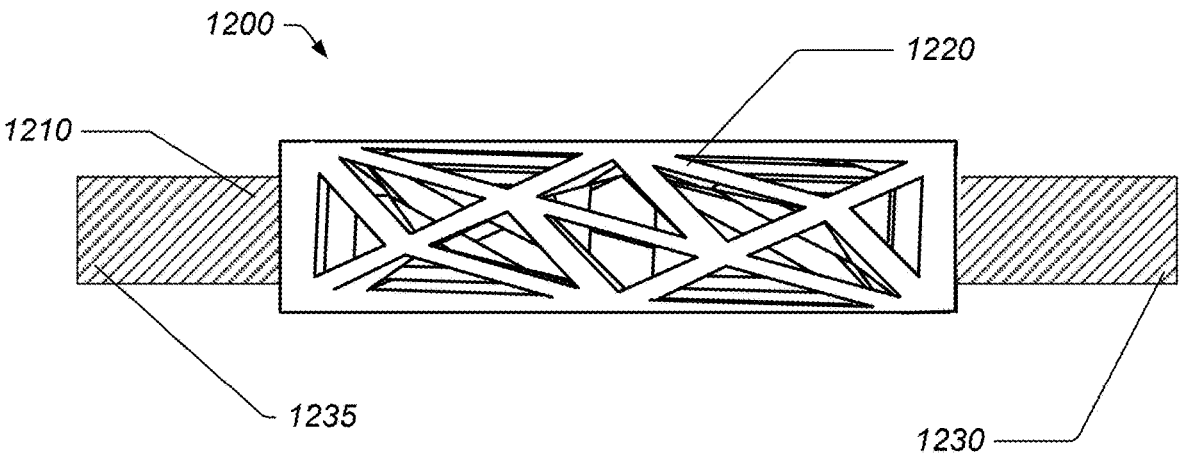
FIG. 14 depicts an embodiment of a bone rod connected to a space truss.

In some fractures of the long bones, the best way to align the bone ends is by inserting a rod or nail through the hollow center of the bone that normally contains some marrow. Most bone rods, however, are poorly adsorbed by the bone, being typically formed from a bio-inert material. In an embodiment, depicted in FIG. 14, an implant 1200 includes a bone rod 1210 at least partially encompassed by a space truss 1220. During use, ends 1230 and 1235 of implant 1200 may be inserted into the bone. Space truss 1220 may also be inserted into the bone, or may occupy an empty space between the broken bone pieces. Space truss 1220 allows better integration of the bone rod into the subject's bone structure.

Figure 15:
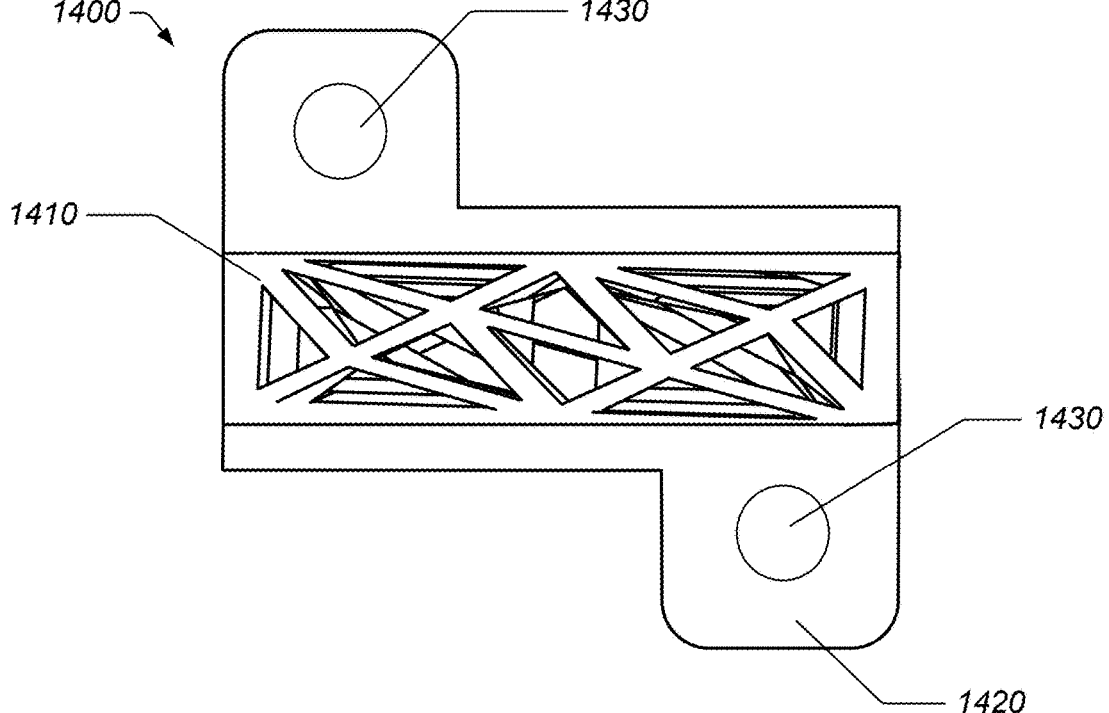
FIG. 15 depicts a top view of an embodiment of an implant which includes a web structure connected to a plate.

FIG. 15 depicts a top view of an embodiment of an implant 1400 which includes a web structure 1410 connected to a plate 1420. Plate 1420 includes one or more screw holes 1430 which allow a bone screw to be used to secure implant 1400 to an exterior of the bone. In use, web structure 1410 may be placed in a space formed in a bone, a natural space (e.g., as a spinal disk replacement device, or between two separated bone segments. In any application, plate 1420 will rest on the exterior of the bone, and provides two screw holes 1430 that allow the user to secure the implant to the bone. In this manner, the implant is less likely to be pulled from the bone section during normal movement of the subject.

Figure 16A:
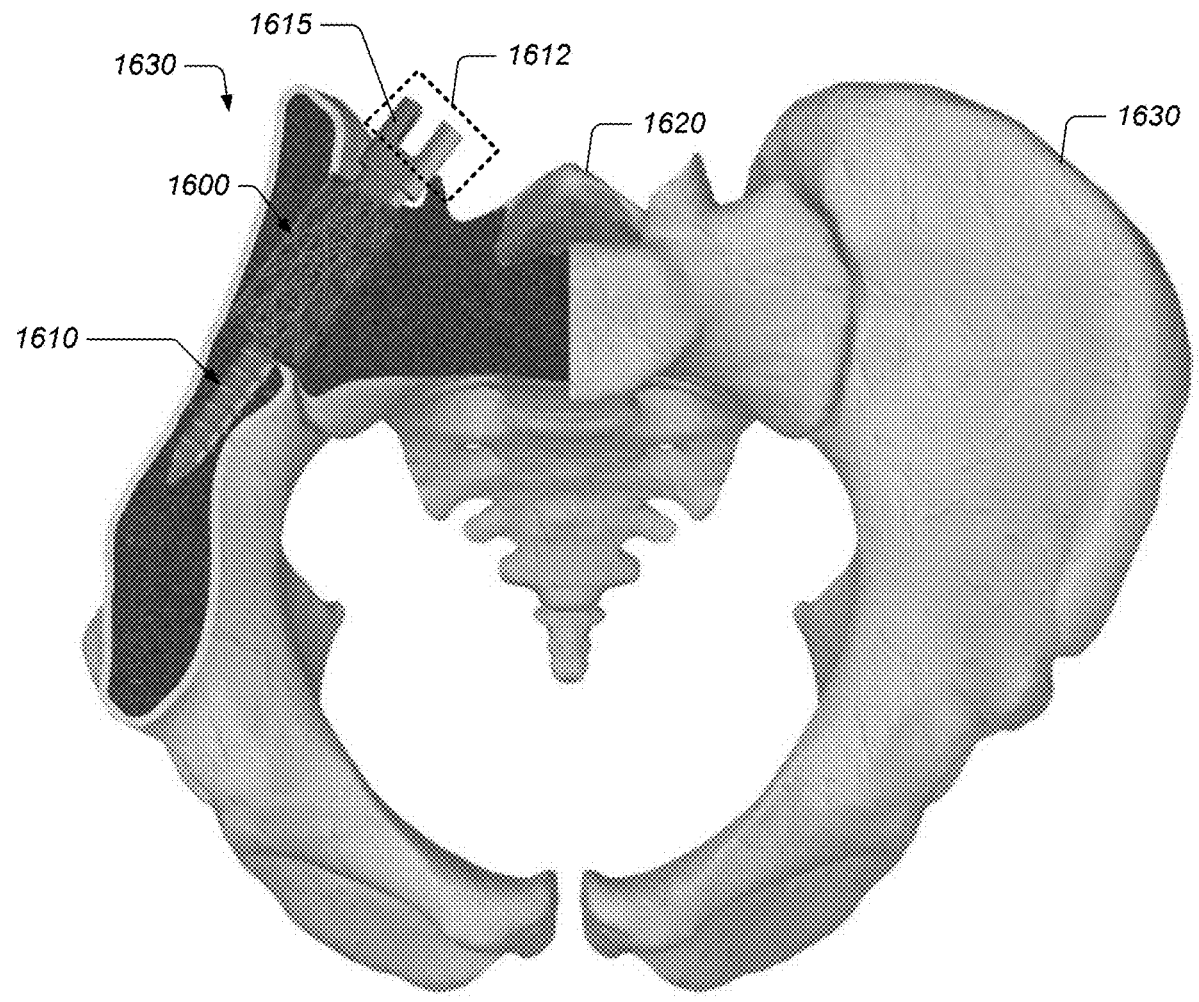
FIG. 16A depicts an SI joint implant placed between the sacrum and the ilium.

FIG. 16A depicts an SI fusion implant 1600 placed between the sacrum and the ilium. In FIG. 16A, the sacrum and the ilium are referenced generally by sacrum 1620 and ilium 1630. In some embodiments, implant 1600 is a solid geometric structure with opening 1640 formed longitudinally through the geometric structure. For example, implant 1600 may be cylindrical, rectilinear, or have a geometric cross-section that includes 3 or more sides (such as triangle, square, pentagon, hexagon, etc.). In certain embodiments, implant 1600 is a cylindrical or tubular structure with opening 1640 extending longitudinally through the structure. Implant 1600 may be, for example, a titanium cylindrical structure. In some contemplated embodiments, implant 1600 includes surface modifications or other structures that allow and/or promote osteointegration between the implant and bone tissue. For example, wall(s) of implant 1600 may have surface roughness from the macro to nano scale that allows and/or promotes osteointegration. As another example, wall(s) of implant 1600 may include fenestrations (e.g., holes or pores) that allow and/or promote osteointegration between the implant and the bone tissue. Combinations of surface modifications (e.g., roughening) and other structures (e.g., fenestrations) may also be contemplated.

The SI fusion implant 1600, in one embodiment, includes a truss implant as described herein. For example, a truss implant as depicted in FIGS. 10A-C, appropriately sized to fit in a cavity formed in the sacrum and ilium bones, may be used to form an SI joint fusion. A fastener 1610, such as a pedicle or S2AI screw, may be inserted through truss implant 1600. To accommodate the fastener 1610, the implant may have a central opening extending through the implant, as shown in FIGS. 16B-D.

Figures 16B, 16C, 16D:
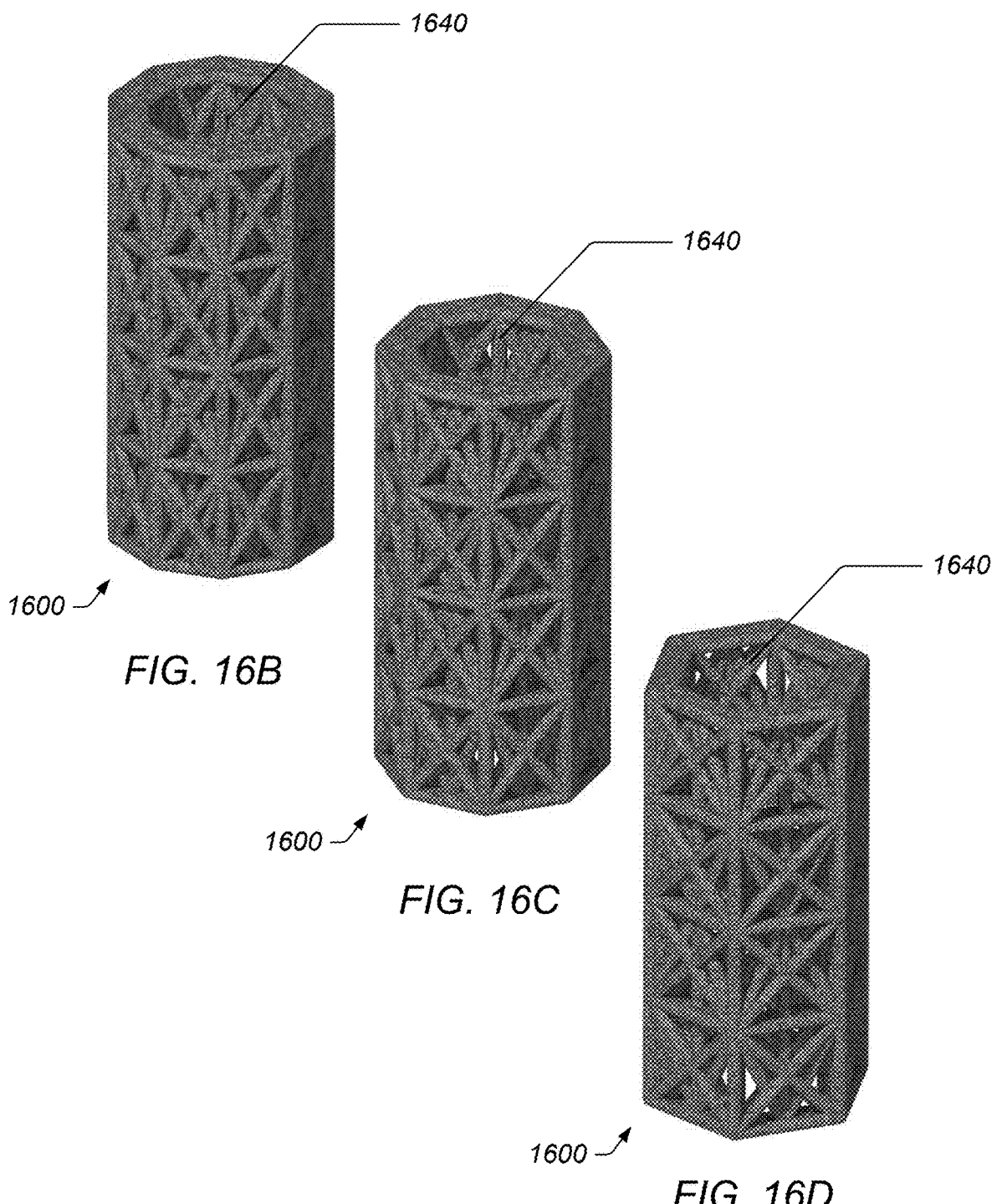
FIGS. 16B-16D depict various embodiments of an SI joint implant.

Referring to FIGS. 16B-D, in some embodiments, the SI fusion implant 1600 has a generally longitudinal (e.g., cylindrical) shape with a central opening 1640 extending longitudinally through the implant. In the illustrated embodiments, the implant is formed from a truss structure optimized for distributing stress on the implant. The truss structure promotes bone growth through the implant allowing the implant to be absorbed into the sacrum and ilium (e.g., sacrum 1620 and ilium 1630, shown in FIG. 16A). The opening 1640 extending longitudinally through the center of the implant 1600 may be round or any of various geometric shapes. The implant 1600 may be designed to have a decagon shaped longitudinal opening (FIG. 16B), an octagon shaped opening (FIG. 16C), or a hexagon shaped opening (FIG. 16D), to name of few of the possible geometrically shaped openings. As another example, implant 1600 may have a triangular shape, a rectangular shape, or any higher order polygon shape.

In an embodiment, an SI joint fusion implant 1600 is implanted between the articulating surfaces of the SI-joint. Initially, a channel (such as at least a hole or cavity) is formed in both the sacrum 1620 and ilium 1630 bones such that the channel spans the SI joint, as shown in FIG. 16A. The truss structure implant 1600, is then placed into the channel. Once in place, one or more fasteners 1610 may be inserted through the sacrum 1620, the implant 1600, and the ilium 1630. A distal end of fasteners 1610 may purchase in the bone tissue as the fastener is tightened (e.g., rotated). In some embodiments, the purchase of the fasteners 1610 pulls the proximal (head) end of the fastener towards implant 1600. For example, the fasteners 1610 may be used to hold the implant 1600 in place and to pull the sacrum 1620 and the ilium 1630 together to initiate bone fusion. In one embodiment, one or more fasteners 1610 are passed through the subject's sacrum bone, the one or more channels, and the subject's ilium such that the ilium 1630 and sacrum 1620 bones are pulled together against the implant 1600. In some embodiments, one or more of implant 1600 or fastener 1610 do not cross the SI joint and/or into the ilium depending on the desired treatment of the subject.

In certain embodiments, fastener 1610 includes head 1615. Head 1615 may be, for example, a screwhead or other head that allows tightening (e.g., rotating) of fastener 1610. In some embodiments, head 1615 may is a tulip shaped head. Head 1615 may, however, have other shapes. Head 1615 may be connected to implant 1600 when the fastener is inserted into the implant such that the head pulls the implant against the ilium 1630 and sacrum 1620 bones.

In some instances, the proximal end of fastener 1610 (e.g., head 1615) may have some motion (e.g., micromotion) relative to implant 1600 after being inserted into the implant. This micromotion may cause pain, which can be uncomfortable for the subject. In certain embodiments, head 1615 is secured to minimize the motion and alleviate pain for the subject. For example, in the illustrated embodiment, locking mechanism 1612 may be coupled to head 1615 to secure the head and prevent motion between the proximal end of fastener 1610 and implant 1600. Locking mechanism 1612 may be, for example, a locking device or other mechanism that secures the proximal end of fastener 1610 to implant 1600. For instance, in some embodiments, locking mechanism 1612 includes a device that is securable to implant 1600 while holding head 1615 in place relative to the implant.

S2AI screws have become the favored method for distal fixation to the pelvis in long or complex spinal reconstruction constructs. Violation of the SI joint by S2AI screw placement changes the motion across the sacroiliac joint. Subsequently, there is a high rate of sacroiliac joint disruption and a high rate of associated sacroiliac joint pain, which may often require on going treatment. The ongoing treatment may include: therapy, medication, injections, and often revision surgery.

The method described herein is for concomitant SP and SI joint fusion that is performed in a similar fashion to S2AI screw placement. The method may begin by using familiar, anatomical landmarks on the dorsal aspect of the sacrum and familiar screw/implant placement techniques. However, in addition to placement of sacropelvic fixation, via the S2AI screw, an additional implant is placed across the sacroiliac joint. Through this cannulated sacroiliac joint fixation device, the S2AI screw is placed, thereby fixing to the ilium via the S2AI screw technique, as well as fusing the SI joint via the sacroiliac implant. The S2AI screw placement technique may be familiar to many spinal surgeons that deal with deformity and/or complex revisions. The modified technique for placement of concomitant sacroiliac joint fixation is described below.

Figure 17:
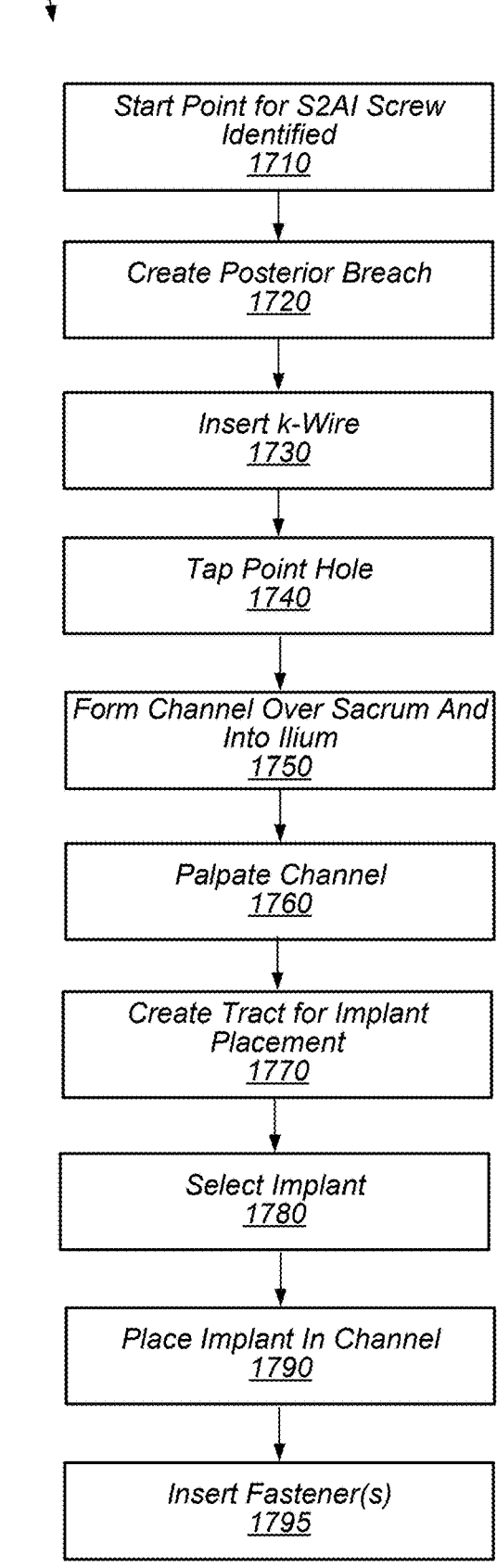
FIG. 17 illustrates a flowchart of a method for implanting an SI fusion implant with a fastener, according to some embodiments.

FIG. 17 illustrates a flowchart of a method for implanting an SI fusion implant 1600 with a fastener 1610, according to some embodiments. It should be noted that in various embodiments of the methods described below, one or more of the elements described may be performed concurrently, in a different order than shown, or may be omitted entirely. Other additional elements may also be performed as desired. In some embodiments, a portion or the entire method may be performed automatically by a computer system.

In method 1700, following normal posterior based exposure, the SI posterior foramina are identified and then the start point for the S2AI screw are identified in 1710. That start point is typically on the dorsum of the sacrum, just lateral and distal to the S1 posterior foramina. A burr is used to create a posterior cortical breach in 1720. For example, a long (e.g., 3.2 millimeter) drill may be used to cannulate through the sacrum. The trajectory is towards the palpable, greater trochanter and the anterior superior iliac spine. The drill hole is verified using a long ball tip sounder. The borders of the drill hole are palpated, including medial, lateral, distal, superior and inferior. A k-wire is then inserted through the pilot hole in 1730. The depth of the pilot hole can be determined by placing an additional k-wire next to the wire in the pilot hole and measuring the difference. This determines the screw length for the S2AI screw. In certain embodiments, the screw length is at least 85 mm. 100 mm is a common length selected. The point hole is tapped over the k-wire in 1740. The k-wire can be brought in and out of the pilot hole by a few centimeters as the hole is tapped to assure that the tap is following the track of the initial pilot hole and k-wire. This tap assures distal fixation in the anterolateral aspect of the ilium. This may be the primary purchase point for either a fully threaded or partially threaded S2AI screw.

Now, the process for sacroiliac joint fusion is undertaken beginning in 1750. This includes drilling over the sacrum and into the ilium in 1750 to form a channel (e.g., hole) in the sacrum bone. The channel may be formed using the pilot hole using the k-wire as a guide. The channel may span the sacroiliac joint and extend into the ilium bone. The drilling into the ilium may be approximately 4-6 centimeters. This channel/hole is then palpated with a ball tip probe in 1760. An undersized brooch is then used to create the tract for placement of the sacroiliac joint fixation implant in 1770. This square brooch should have one flat surface facing anterior and inferior to lessen the possibility of anterior breach by one of the corners of the brooch and subsequent implant. This expanded tract proximally in the S2AI trajectory may be palpated with a ball probe. The tract is measured for length and an appropriate size implant (as described herein) is selected in 1780. The implant is then placed in the channel in 1790. For instance, the implant may be impacted down the S2AI tract, through the sacrum into the ilium. In some embodiments, the implant is countersunk. One or more fasteners may be inserted through (e.g., passed through) the sacrum bone, the longitudinal opening of the implant, and into the subject's ilium bone in 1795 (and as shown in FIG. 16A). The inserting through of the fasteners may pull together the ilium and sacrum bones. In various embodiments, the longitudinal opening of the implant is configured to be large enough to accommodate passage of the fastener (e.g., a pedicle screw or an S2AI screw), which is then placed over the wire. Distal fixation is assured via the distal threads of the long fastener. The position of the k-wire and brooch, and subsequently, the fastener itself, as well as the sacroiliac joint fixation device can be checked on multiple radiographic views, including AP, lateral, and teardrop views. In certain embodiments, in 1797, a locking mechanism (e.g., locking mechanism 1612) is secured to the fastener(s) (e.g., fastener 1610) and the implant (e.g., implant 1600).

In one embodiment, a diameter and/or length of the struts of an SI joint implant 1600 are predetermined such that, when the web structure is in contact with the bone structure, BMP production from osteoblasts adhering to the implant surface is achieved. In various embodiments, the diameter and/or length of the struts is predetermined such that at least a portion of the struts create a microstrain in cellular material, bony structure, or tissue adhered to the struts (e.g., adhered osteoblasts, bone matrix, or lamellar tissue) of between about 1 microstrain ($\mu\varepsilon$) and about 5000 microstrain ($\mu\varepsilon$), between about 500 pe and about 2000 pe, or between about 1000$\mu\varepsilon$ and about 1500$\mu\varepsilon$. In some embodiments, the diameter and/or length of the struts is predetermined such that at least a portion of the struts create a change in length of the adhered osteoblasts, bone matrix, or lamellar tissue of between about 0.05% and about 0.2% or between about 0.1% and about 0.15%.

An SI joint implant may be prepared having struts of a length of between about 1 to 100 mm. The diameter of the struts may be set such that the strut undergoes a change of length of between about 0.05% and about 0.2% when the web structure is in contact with the bone structure. In some embodiments, the diameter of the struts is predetermined such that the strut undergoes a change of length of between about 0.000125% and 0.0005% or between about 0.00025% and 0.000375%.

Implants may be modified such that at least a portion of the struts that form the web structure produce the appropriate microstrain/lengthening of adhered osteoblasts. In some embodiments, most, if not all, of the struts that form the web structure of an implant may be 'programmed' (or designed) to stimulate BMP production. In other embodiments, some struts may be programmed/designed for BMP production, while other struts have different physical properties than the programmed struts.

In various embodiments, an SI joint implant may be optimized to distribute stresses encountered by the implant. An SI joint implant is typically subjected to non-uniform stress. The non-uniform stress creates different forces across the implant. If an implant is designed to withstand a certain homogenous force, the implant may fail when subjected to non-uniform stress. In a non-uniform stress situation, some of the stress on the implant may be enough to deform the implant. It is desirable to have an implant that is customized to the expected non-uniform stress that will be encountered in the bone structure being repaired.

In accordance with the above descriptions, in various embodiments, an implant may include a web structure. The web structure for the implant may include a micro truss design. In some embodiments, the micro truss design may include a web structure with multiple struts. Other web structures are also contemplated. The web structure may extend throughout the implant (including a central portion of the implant). The web structure may thus reinforce the implant along multiple planes (including internal implant load bearing) and provide increased area for bone graft fusion. The web structure may be used in implants such as spinal implants, corpectomy devices, hip replacements, knee replacements, long bone reconstruction scaffolding, and cranio-maxifacial implants. Other implant uses are also contemplated. In some embodiments, the web structure for the implant may include one or more geometric objects (e.g., polyhedrons). In some embodiments, the web structure may not include a pattern of geometrical building blocks (e.g., an irregular pattern of struts may be used in the implant). In some embodiments, the web structure may include a triangulated web structure including two or more tetrahedrons. A tetrahedron may include four triangular faces in which three of the four triangles meet at each vertex. The web structure may further include two tetrahedrons placed together at two adjacent faces to form a web structure with a hexahedron-shaped frame (including six faces). In some embodiments, multiple hexahedron-shaped web structures may be arranged in a side-by-side manner. The web structures may connect directly through side vertices (e.g., two or more hexahedron-shaped web structures may share a vertex). In some embodiments, the web structure may be angled to provide lordosis to the implant.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. For example, although in certain embodiments, struts have been described and depicts as substantially straight elongated members, struts may also include elongated members curved/arched along at least a portion of their length. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. Furthermore, it is noted that the word "may" is used throughout this application in a permissive sense (i.e., having the potential to, being able to), not a mandatory sense (i.e., must). The term "include", and derivations thereof, mean "including, but not limited to". As used in this specification and the claims, the singular forms "a", "an" and "the" include plural referents unless the content clearly indicates otherwise. Thus, for example, reference to "a strut" includes a combination of two or more struts. The term "coupled" means "directly or indirectly connected".

What is claimed is:

1. An implant apparatus, comprising:
   an implant configured to interface with bone tissue in a sacroiliac joint of a subject, and wherein the implant is configured to be placed in a channel formed in a sacrum bone of the subject;
   an opening formed longitudinally through the implant; and
   a single body fastener configured to be inserted through the opening of the implant and into the bone tissue beyond a distal end of the implant while the implant is in place in the channel, wherein, as the fastener is inserted through the opening, a distal end of the fastener extends into and purchases directly within the bone tissue of the sacroiliac joint to secure the implant within the bone tissue.

2. The implant apparatus of claim 1, wherein the fastener is configured to be inserted through the sacrum bone and into the subject's ilium bone.

3. The implant apparatus of claim 1, wherein the fastener, when inserted, purchases the bone tissue beyond the distal end of the implant.

4. The implant apparatus of claim 1, wherein the channel spans the sacroiliac joint and extends into an ilium bone of the subject.

5. The implant apparatus of claim 1, wherein a geometric cross-section of the implant includes 3 or more sides.

6. The implant apparatus of claim 1, wherein the implant is a cylindrical structure.

7. The implant apparatus of claim 1, wherein the implant is a rectilinear structure.

8. The implant apparatus of claim 1, wherein an outer surface of the implant has a surface roughness from the macro to nano scale.

9. The implant apparatus of claim 1, wherein the implant includes a space truss comprising two or more planar truss units having a plurality of struts joined at nodes.

10. The implant apparatus of claim 9, wherein at least one of the planar truss units comprises one or more planar triangular truss units having three substantially straight struts and three nodes in a triangular configuration.

11. The implant apparatus of claim 9, wherein the two or more planar truss units are coupled to one another such that at least one planar truss unit lies in a plane that is not substantially parallel to a plane of at least one other planar truss unit that shares at least one strut with the at least one planar truss unit.

12. The implant apparatus of claim 9, wherein the two or more planar truss units define an exterior surface of the implant.

13. The implant apparatus of claim 9, wherein at least some of the struts define triangular trusses having at least one node shared by two different triangular planar truss units having different corresponding angles.

14. The implant apparatus of claim 9, wherein a diameter and a length of the struts in the implant are predetermined to create microstrain in adjacent cellular material, osteoblasts, bone matrix, or lamellar tissue adhered to the struts.

15. The implant apparatus of claim 9, wherein a diameter of the struts in the cylindrical structure is predetermined such that a length of the struts in the cylindrical structure undergoes a change of length of between about 0.05% and about 0.2% when the cylindrical structure is in contact with the bone tissue.

16. The implant apparatus of claim 1, wherein the implant is sized based on a size of the channel.

17. An implant apparatus, comprising:
an implant configured to interface with bone tissue in a sacroiliac joint of a subject, and wherein the implant is configured to be placed in a channel formed only in a sacrum bone of the subject;
an opening formed longitudinally through the implant;
a fastener configured to be inserted through the opening of the implant and into the bone tissue beyond a distal end of the implant while the implant is in place in the channel, wherein a distal end of the fastener purchases within bone tissue of an ilium bone of the subject beyond a distal end of the channel to secure the implant within the bone tissue of the ilium bone; and
a locking mechanism configured to be coupled to a proximal end of the fastener, wherein the locking mechanism secures the proximal end of the fastener to the implant.

18. The implant apparatus of claim 17, wherein the fastener includes a head configured to allow rotation of the fastener while inserting the fastener through the implant, and wherein the locking mechanism is configured to be coupled to the head of the fastener to hold the head in place relative to the implant.

19. The implant apparatus of claim 17, wherein the fastener is configured to be inserted through the sacrum bone and into the subject's ilium bone.

20. The implant apparatus of claim 17, wherein the fastener is configured to extend through the opening of the implant and purchase bone tissue beyond the distal end of the implant.

21. A method, comprising:
obtaining an implant having an opening formed longitudinally through the implant;
forming a channel in a sacrum bone of the subject;
placing the implant into the channel such that the implant interfaces with bone tissue in a sacroiliac joint of a subject;
inserting a fastener through the opening of the implant while the implant is in place in the channel; and
rotating the fastener to purchase a distal end of the fastener within the bone tissue beyond a distal end of the implant while the implant is in place in the channel and secure the implant within the bone tissue.

22. The method of claim 21, wherein forming the channel in the sacrum bone includes drilling over the sacrum bone and into the ilium bone.

23. The method of claim 21, further comprising palpating the channel before placing the implant into the channel.

24. The method of claim 21, further comprising creating a tract for the implant in the channel before placing the implant into the channel.

25. The method of claim 21, wherein placing the implant into the channel includes impacting the implant into the channel.

26. The method of claim 21, wherein the implant is countersunk into the channel.

27. The method of claim 21, further comprising securing a locking mechanism to a proximal end of the fastener, wherein the locking mechanism secures the proximal end of the fastener to the implant.

28. The implant apparatus of claim 1, wherein the distal end of the fastener extends into and purchases in the bone tissue beyond a distal end of the channel as the fastener is inserted through the opening.

29. The implant apparatus of claim 17, wherein the locking mechanism is secured to the implant around a head of the fastener to inhibit movement of the head of the fastener relative to the implant.

30. The method of claim 21, wherein rotating the fastener moves the distal end of the fastener into bone tissue beyond a distal end of the channel with the distal end of the fastener purchasing in the bone tissue as the fastener is secured to the implant.

* * * * *